US008785612B2

(12) United States Patent
Davies et al.

(10) Patent No.: US 8,785,612 B2
(45) Date of Patent: Jul. 22, 2014

(54) SUGARCANE BACILLIFORM VIRAL (SCBV) ENHANCER AND ITS USE IN PLANT FUNCTIONAL GENOMICS

(75) Inventors: John P. Davies, Portland, OR (US); Vaka S. Reddy, Beaverton, OR (US); William M. Ainley, Carmel, IN (US); Mark A. Thompson, Zionsville, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 32 days.

(21) Appl. No.: 13/220,564

(22) Filed: Aug. 29, 2011

(65) Prior Publication Data

US 2012/0054908 A1    Mar. 1, 2012

Related U.S. Application Data

(60) Provisional application No. 61/402,570, filed on Aug. 30, 2010.

(51) Int. Cl.
*C12N 15/00* (2006.01)
*C12N 15/09* (2006.01)
*C12N 15/113* (2010.01)
*C12N 5/04* (2006.01)
*C12N 15/82* (2006.01)

(52) U.S. Cl.
USPC ....... 536/24.1; 800/278; 800/298; 800/300.1; 800/303; 435/468; 435/410; 435/412; 435/320.1

(58) Field of Classification Search
None
See application file for complete search history.

(56) References Cited

U.S. PATENT DOCUMENTS

| 5,981,840 | A  | * | 11/1999 | Zhao et al. | 800/294 |
| 6,395,962 | B1 | * | 5/2002 | Vance | 800/278 |
| 2012/0060238 | A1 | * | 3/2012 | Davies et al. | 800/291 |

FOREIGN PATENT DOCUMENTS

| AU | WO-0242450 A | * | 5/2002 |
| CN | 1276014 A | | 12/2000 |
| WO | WO9909190 A1 | | 2/1999 |
| WO | WO 02/42450 | | 5/2002 |
| WO | WO 2010/086277 | | 8/2010 |

OTHER PUBLICATIONS

Braithwaite et al. A variable region of the Sugarcane Bacilliform Virus (SCBV) genome can be used to generate promoters for the transgene expression in sugarcane. Plant Cell Rep. 2004. 23: 319-326.*
Al-Saadi, "Analysis of the Sugarcane Bacilliform Virus in Both Monocots and Dicots." Jan. 1, 2002. XP002662962 (2 pages).
Al-Saady et al., "Deletion Analysis of the Sugarcane bacilliform virus Promoter Activity in Monocot and Dicot Plants," *Biotechnology*, 9(3): 283-293, 2010.

(Continued)

*Primary Examiner* — Cathy Kingdon Worley
*Assistant Examiner* — Ashley K Buran
(74) *Attorney, Agent, or Firm* — Marcos P. Rivas; Klarquist Sparkman, LLP

(57) ABSTRACT

Identification of new enhancer sequence has significant utility in the plant functional genomics. The sugarcane bacilliform badnavirus (SCBV) transcriptional enhancer has been identified. This enhancer can be used to increase the rate of transcription from gene promoters and in activation tagging experiments. A ten-fold increase in transcription was observed when a 4x array of the SCBV enhancer was placed upstream of a truncated form of the maize alcohol dehydrogenase minimal promoter. Methods of using the SCBV transcriptional enhancer are described, as are chimeric transcription regulatory regions, constructs, cells, tissues, and organisms that comprise one or more copies of the enhancer.

21 Claims, 5 Drawing Sheets

(56) References Cited

OTHER PUBLICATIONS

Al-Saady et al., "Tissue specificity of the sugarcane bacilliform virus promoter in oat, barley and wheat," *Molecular Breeding*, 14: 331-338, 2004.
Braithwaite et al., "A variable region of the Sugarcane Bacilliform Virus (SCBV) genome can be used to generate promoters for transgene expression in sugarcane," *Plant Cell Rep*, 23: 319-326, 2004.
Schenk et al., "A promoter from sugarcane bacilliform badnavirus drives transgene expression in banana and other monocot and dicot plants," *Plant Molecular Biology*, 39: 1221-1230, 1999.
Schenk et al., "Promoters for pregenomic RNA of banana streak badnavirus are active for transgene expression in monocot and dicot plants," *Plant Molecular Biology*, 47: 399-412, 2001.
Bouchez et al., "The ocs-element is a component of the promoters of several T-DNA and plant viral genes," *EMBO Journal*, 8(13): 4197-4204, 1989.
Ellis et al., "The *ocs* element: a 16 base pair palindrome essential for activity of the octopine synthase enhancer," *EMBO Journal*, 6(11): 3203-3208, 1987.
Geijskes et al., "Sequence analysis of an Australian isolate of sugarcane bacilliform badnavirus," *Arch. Virol.*, 147: 2393-2404, 2002.
Jeong et al., "T-DNA Insertional Mutagenesis for Activation Tagging in Rice," *Plant Physiology*, 130: 1636-1644, 2002.
Kay et al., "Duplication of CaMV 35S Promoter Sequences Creates a Strong Enhancer for Plant Genes," *Science*, 236: 1299-1302, 1987.
Klein et al., "Transfer of foreign genes into intact maize cells with high-velocity microprojectiles," *Proc. Natl. Acad. Sci. USA*, 85: 4305-4309, 1988.
Ma et al., "Molecular analysis of rice plants harboring a multifunctional T-DNA tagging system," *J. Genet. Genomics*, 36: 267-276, 2009.
Mathews et al., "Activation Tagging in Tomato Identifies a Transcriptional Regulator of Anthocyanin Biosynthesis, Modification, and Transport," *The Plant Cell*, 15: 1689-1703, 2003.
Qu et al., "A Versatile Transposon-Based Activation Tag Vector System for Functional Genomics in Cereals and Other Monocot Plants," *Plant Physiology*, 146: 189-199, 2008.
Walker et al., "DNA sequences required for anaerobic expression of the maize alcohol dehydrogenase 1 gene," *Proc. Natl. Acad. Sci. USA*, 84:6624-6628, 1987.
Wan et al., "Activation tagging, an efficient tool for functional analysis of the rice genome," *Plant. Mol. Biol.*, 69: 69-80, 2009.
Weigel et al., "Activation Tagging in *Arabidopsis*," *Plant Physiology*, 122: 1003-1013, 2000.
Supplemental Search Report issued on Jan. 14, 2014, in corresponding Chinese Application No. 201180052649.2 (1 page).

\* cited by examiner

FIG. 1

```
-839
AAGCTTATTGAATGGGAAAACAAATTCTTGATCCATTCCCCAAATTCAAGAAGATATGTTGAAAGAACTGAA

-764  -758
CATATCATGATGGCAACAAGAGCCTACGCTACTATCTGGATGCAGGAAGCCTGCAATCATGTTAACATCAGGA

-689
ACAAGGCTTAATCCTCGTAGAAGATTTTACAAGTGTGCCATGAATATCTGCCACTGCTGGTATTGGGCAGATTTA

-614                           -576
CTTGAAGAATACGTGCCAAGAGAGGATCGAAGATTTCATGGTTGAAAACTTCGACAAGAAAGCAAAGCTGGATGAA

-539                -503
CCAAGTTCATCAAACGTTCACCATGATGATTATGAAGAACACCGTTCGAGTGTCATCAGGCCAAGGCCAAACA

-464
GATGATCATTTCAGACCATGGGGGATGTTACATACTGGCTGAATAAAGAAGCAGAAGAGTGCCACAAGGGGC

-389                                           -333
GACAACGTCGAAGGCGCAGAAGACGCAGTGCGATCTCACTGACCTAAGCAATGACGACCCAGTGGAGAGATCGTAA

-314
GCAATGACGTATGAGCGTGGAGGACCCATGAAAGCACTGAGAAGGCATCTCAACTTCCGTGTGTGAGTGCGCA

-239      -222
TCCTATGCGATGCTTTGTACCTTTGTTAGCTGTGTGTGTCCTTTTGGATCTGTGCCACTTTACCTTTGTCGGCC

-164
ACGTTGCCCTTGCCTTAGCATCTACGCAAGCATAGCGCTCGGCTGGTGTGTGTTCCCTCTGCCTATATAAGGCATG

-89
GTTGTATGACTCTTACACTCATCGGTAGTTCACCACATGAGTATTTGAGTCAAGTTTGGCTTGAATAAGAAT

-14
TACACCTTTCCGCA
```

US 8,785,612 B2

SUGARCANE BACILLIFORM VIRAL (SCBV) ENHANCER AND ITS USE IN PLANT FUNCTIONAL GENOMICS

PRIORITY CLAIM

This application claims priority to and the benefit of U.S. Provisional Application No. 61/402,570, filed Aug. 30, 2010. The entire disclosure of U.S. Provisional Application No. 61/402,570 and of International Application No. PCT/US2011/049532, filed Aug. 29, 2011, are incorporated herein by reference in their entirety.

FIELD

The disclosure relates to the field of plant molecular biology and genetic engineering, and specifically to polynucleotide molecules useful for modulating (e.g., enhancing) gene expression and/or protein production in plants.

PARTIES TO JOINT RESEARCH AGREEMENT

This application describes and claims certain subject matter that was developed under a written joint research agreement between Agrigenetics, Inc., Mycogen Corporation, Exelixis Plant Sciences, Inc., and Exelixis, Inc., having an effective date of Sep. 4, 2007.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Aug. 27, 2011, and having a size of ~1.6 kilobytes, as permitted under 37 CFR 1.821(c). The material in the aforementioned file is hereby incorporated by reference in its entirety.

BACKGROUND

There is an on-going need for genetic regulatory elements that direct, control or otherwise regulate expression of a transcribable nucleic acid (e.g., a transgene), for instance for use in a genetically engineered organism such as a plant. Genetic regulatory elements typically include 5' untranslated sequences such a transcription initiation regions that contain transcription factor and RNA polymerase binding site(s), enhancer/silencer elements, a TATA box and a CAAT box together with 3' polyadenylation sequences, transcription stop signals, translation start and stop signals, splice donor/acceptor sequences and the like.

For the purposes of genetic engineering, genetic regulatory elements are typically included in an expression vector or other engineered construct, to regulate expression of a transgene operably linked to the regulatory elements. Well known examples of promoters used in this fashion are CaMV35S promoter (Nagy et al. In: *Biotechnology in plant science: relevance to agriculture in the eighties*. Eds. Zaitlin et al. Academic Press, Orlando, 1985), maize ubiquitin promoter (Ubi; Christensen & Quail, *Transgenic Research* 5:213, 1996) and the Emu promoter (Last et al., *Theor. Appl. Genet.* 81581, 1991), though many others will be known to those of ordinary skill. Likewise, enhancers have been isolated from various sources for use in genetic engineering; these include the cauliflower mosaic virus (35S CaMV) enhancer, a figwort mosaic virus (FMV) enhancer, a peanut chlorotic streak caulimovirus (PClSV) enhancer, or mirabilis mosaic virus (MMV) enhancer.

There is an on-going need to identify genetic regulatory elements, such as enhancer domains, that can be harnessed to control expression of sequences operably linked thereto, for instance in heterologous nucleic acid molecules such as vectors and other engineered constructs.

SUMMARY OF THE DISCLOSURE

The present disclosure describes novel transcription regulatory regions comprising an enhancer domain and, under the enhancing control of the enhancer domain, a transcription regulatory domain. The enhancer domain comprises a plurality (e.g., two to four or more) of copies of a natural but previously unrecognized SCBV enhancer arranged in tandem. The transcription regulatory regions (promoters) of the present disclosure provide enhanced transcription as compared to the promoter in the absence of the enhancer domain. In one example, a chimeric transcription regulatory region is disclosed comprising one or more copies of the SCBV enhancer element shown in position 337 to position 618 of SEQ ID NO: 1; and operably linked thereto, a promoter comprising an RNA polymerase binding site and a mRNA initiation site, wherein when a nucleotide sequence of interest is transcribed under regulatory control of the chimeric transcription regulatory region, the amount of transcription product is enhanced compared to the amount of transcription product obtained with the chimeric transcription regulatory region comprising the promoter and not comprising the SCBV enhancer sequence.

DNA constructs are also provided comprising a described transcription regulatory region and a DNA sequence to be transcribed. In one example, a DNA construct comprises a disclosed transcriptional initiation region operably linked to a transcribable polynucleotide molecule operably linked to a 3' transcription termination polynucleotide molecule. The DNA constructs provide for enhanced transcription of the DNA sequence to be transcribed. Transgenic plants, plant cells or tissue (such as a dicotyledon or a monocotyledon plants, plant cells or tissue) transformed with the disclosed constructs are also disclosed. Also provided is a plant seed, fruit, leaf, root, shoot, flower, cutting and other reproductive material useful in sexual or asexual propagation, progeny plants inclusive of F1 hybrids, male-sterile plants and all other plants and plant products derivable from the disclosed transgenic plant. Methods of producing the disclosed transgenic plants, plant cells or tissue are also provided herein.

The foregoing and other features of the disclosure will become more apparent from the following detailed description, which proceeds with reference to the accompanying figures.

BRIEF DESCRIPTION OF THE DRAWINGS

FIG. 1 shows the sequence of the SCBV promoter (corresponding to positions 6758-7596 of GenBank Accession No. AJ277091.1, "Sugarcane bacilliform IM virus complete genome, isolate Ireng Maleng" which incorporated by reference herein in its entirety as it appeared on-line on Apr. 15, 2010); this sequence is also shown in SEQ ID NO: 1. The enhancer sequences defined in this study extend from −222 to −503 and are underlined in the Figure (corresponding to position 337 to position 618 of SEQ ID NO: 1).

FIG. 2A shows fragments of the SCBV promoter containing sequences from −839 bp, −576 by and −333 by upstream of the transcription start site and 106 by downstream of the transcription start site fused to the luciferase (LUC) reporter gene. FIG. 2B shows a histogram of the ratio of LUC/GUS activity from HiII cells co-transformed with the plasmids above and a UBI::GUS reporter construct. The results show that the promoter fragment containing sequences from −576 by upstream of the transcription start site had 60% of the activity of the promoter fragment containing 839 by upstream of the start site. In contrast, the promoter fragment containing sequences from −333 by upstream of the start site had only 10% of the activity of the full-length promoter (from −839 by upstream of the transcription start site). Thus, sequences involved in promoter activity reside upstream of the −333 bp.

As shown in FIG. 3B, constructs containing 1, 2 and 4 copies of the SCBV enhancer had more than 5 times, 6 times and 10 times more activity, respectively, than did cells bombarded with the truncated Adh1 construct without any enhancers. The 4×MMV construct had 2.5 times the activity as the truncated Adh1 construct and the 2×MMV 2×SCBV construct had 6 times the activity as the truncated Adh1 construct.

SEQUENCE LISTING

Figure 2A:
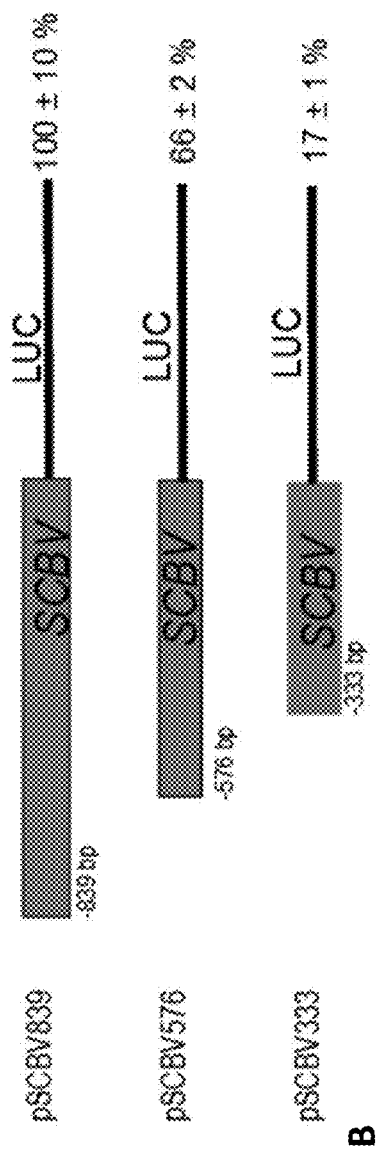
FIGS. 2A and 2B illustrate results of the analysis of the SCBV promoter.
Figure 2B:
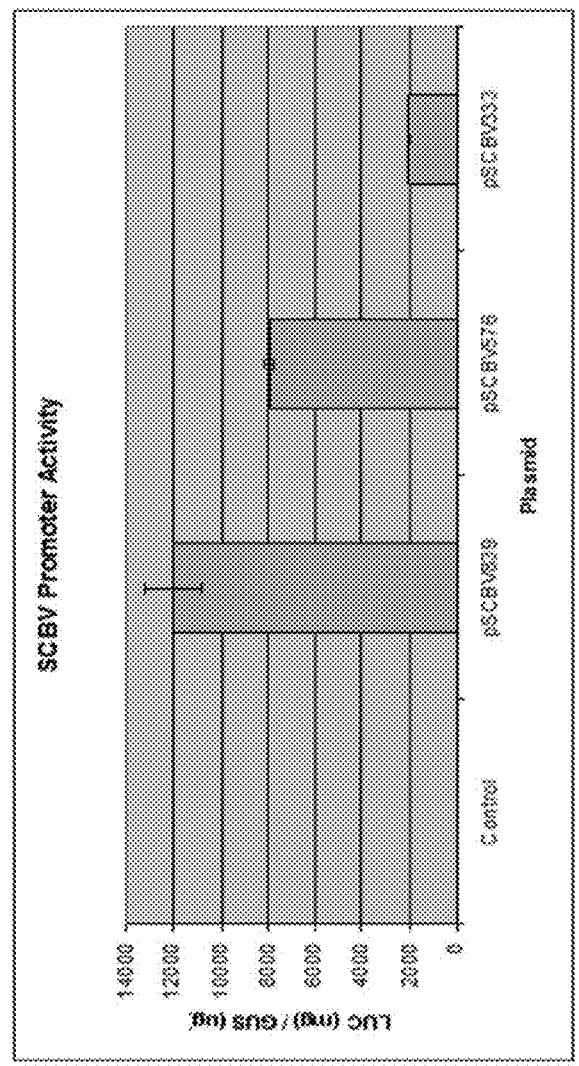

The nucleic and/or amino acid sequences listed in the sequence listing below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. Nucleic acid sequences (in the Sequence Listing or elsewhere herein) are presented in the standard 5' to 3' direction, and protein sequences are presented in the standard amino (N) terminal to carboxy (C) terminal direction.

SEQ ID NO: 1 shows the nucleic acid sequence of the SCBV promoter (corresponding to positions 6758-7596 of GenBank Accession No. AJ277091.1, "Sugarcane bacilliform IM virus complete genome, isolate Ireng Maleng" incorporated by reference herein in its entirety as it appeared on-line on Apr. 15, 2010).

The enhancer elements described herein are from position 337 to position 618 of SEQ ID NO: 1.

DETAILED DESCRIPTION

I. Abbreviations

3' UTR 3'-untranslated region
5' UTR 5'-untranslated region
Adh1 alcohol dehydrogenase 1
asRNA antisense RNA
cDNA complementary DNA
dsRNA double-stranded RNA
GAPDH glyceraldehyde 3-phosphate dehydrogenase
KB kilobytes
kbp kilobase pairs
LUC luciferase
miRNA microRNA
nt nucleotide
ORF open reading frame
PCR polymerase chain reaction
RT-PCR reverse transcription and PCR
SCBV sugarcane bacilliform virus
siRNA small interfering RNA
ssRNA single stranded RNA
$T_m$ thermal melting point
UTR untranslated region II. Terms Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

5' and/or 3': Nucleic acid molecules (such as, DNA and RNA) are said to have "5' ends" and "3' ends" because mononucleotides are reacted to make polynucleotides in a manner such that the 5' phosphate of one mononucleotide pentose ring is attached to the 3' oxygen of its neighbor in one direction via a phosphodiester linkage. Therefore, one end of a polynucleotide is referred to as the "5' end" when its 5' phosphate is not linked to the 3' oxygen of a mononucleotide pentose ring. The other end of a polynucleotide is referred to as the "3' end" when its 3' oxygen is not linked to a 5' phosphate of another mononucleotide pentose ring. Notwithstanding that a 5' phosphate of one mononucleotide pentose ring is attached to the 3' oxygen of its neighbor, an internal nucleic acid sequence also may be said to have 5' and 3' ends.

In either a linear or circular nucleic acid molecule, discrete internal elements are referred to as being "upstream" or 5' of the "downstream" or 3' elements. With regard to DNA, this terminology reflects that transcription proceeds in a 5' to 3' direction along a DNA strand. Promoter and enhancer elements, which direct transcription of a linked gene, are generally located 5' or upstream of the coding region. However, enhancer elements can exert their effect even when located 3' of the promoter element and the coding region. Transcription termination and polyadenylation signals are located 3' or downstream of the coding region.

Agronomic trait: Characteristic of a plant, which characteristics include, but are not limited to, plant morphology, physiology, growth and development, yield, nutritional enhancement, disease or pest resistance, or environmental or chemical tolerance are agronomic traits. An "enhanced agronomic trait" refers to a measurable improvement in an agronomic trait including, but not limited to, yield increase, including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also affected by efficiency of germination (including germination in stressed conditions), growth rate (including growth rate in stressed conditions), ear number, seed number per ear, seed size, composition of seed (starch, oil, protein) and characteristics of seed fill. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this disclosure can also be used to provide plants having improved growth and development, and ultimately increased yield, as the result of modified expression of plant growth regulators or modification of cell cycle or photosynthesis pathways. Additional examples of agronomic traits, and altering such traits in plants, are provided herein and/or will be recognized by those of ordinary skill in the art.

Alterations: Alterations in a polynucleotide (for example, a polypeptide encoded by a nucleic acid of the present invention), as this term is used herein, comprise any deletions, insertions, and point mutations in the polynucleotide sequence. Included within this definition are alterations to the genomic DNA sequence that encodes the polypeptide Likewise, the term "alteration" may be used to refer to deletions, insertions, and other mutations in polypeptide sequences.

Altering level of production or expression: Changing, either by increasing or decreasing, the level of production or expression of a nucleic acid molecule or an amino acid molecule (for example an siRNA, a miRNA, an mRNA, a gene, a polypeptide, a peptide), as compared to a control level of production or expression.

Amplification: When used in reference to a nucleic acid, this refers to techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antisense, Sense, and Antigene: DNA has two antiparallel strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, an RNA transcript will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target. An antisense RNA (asRNA) is a molecule of RNA complementary to a sense (encoding) nucleic acid molecule.

Antisense inhibition: This term refers to a class of gene regulation based on cytoplasmic, nuclear, or organelle inhibition of gene expression (e.g., expression for a host cell genome or the genome of a pathogen, such as a virus) due to the presence in a cell of an RNA molecule complementary to at least a portion of the mRNA being translated.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells or other samples.

Chimeric or Chimera: The product of the fusion of portions of two or more different polynucleotide or polypeptide molecules. For instance, the phrases "chimeric sequence" and "chimeric gene" refer to nucleotide sequences derived from at least two heterologous parts. Chimeric sequence may comprise DNA or RNA.

Chimeric transcription regulatory region: An array of nucleic acid control or regulatory sequences that direct transcription of a nucleic acid operably linked thereto, which array is assembled from different polynucleotide sources. For instance, chimeric transcription regulatory regions as described herein may be produced through manipulation of known promoters or other polynucleotide molecules. Chimeric transcription regulatory regions may combine one or more enhancer domains with one or more promoters, for example, by fusing a heterologous enhancer domain from a first native promoter to a second promoter with its own partial or complete set of regulatory element(s). This disclosure provides, inter alia, chimeric transcription regulatory regions that contain at least one SCBV enhancer domain fused (that is, operably linked) to a promoter active in plant(s).

Construct: Any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more transcribable polynucleotide molecule has been operably linked.

Control plant: A plant that does not contain a recombinant DNA that confers (for instance) an enhanced or altered agronomic trait in a transgenic plant, is used as a baseline for comparison, for instance in order to identify an enhanced or altered agronomic trait in the transgenic plant. A suitable control plant may be a non-transgenic plant of the parental line used to generate a transgenic plant, or a plant that at least is non-transgenic for the particular trait under examination (that is, the control plant may have been engineered to contain other heterologous sequences or recombinant DNA molecules). Thus, a control plant may in some cases be a transgenic plant line that comprises an empty vector or marker gene, but does not contain the recombinant DNA, or does not contain all of the recombinant DNAs, in the test plant.

Cosuppression: The expression of a foreign (heterologous) gene that has substantial homology to an endogenous gene, resulting in suppression of expression of both the foreign and the endogenous gene.

DNA (deoxyribonucleic acid): DNA is a long chain polymer which comprises the genetic material of most organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule includes the reverse complement of that DNA molecule. Except where single-strandedness is required by the text herein, DNA molecules, though written to depict only a single strand, encompass both strands of a double-stranded DNA molecule.

Encode: A polynucleotide is said to encode a polypeptide if, in its native state or when manipulated by methods known to those skilled in the art, the polynucleotide molecule can be transcribed and/or translated to produce a mRNA for and/or the polypeptide or a fragment thereof. The anti-sense strand is the complement of such a nucleic acid, and the encoding sequence can be deduced therefrom.

Enhancer domain: A cis-acting transcriptional regulatory element (a.k.a. cis-element) that confers an aspect of the overall control of gene expression. An enhancer domain may function to bind transcription factors, which are trans-acting protein factors that regulate transcription. Some enhancer domains bind more than one transcription factor, and transcription factors may interact with different affinities with more than one enhancer domain. Enhancer domains can be identified by a number of techniques, including deletion analysis (deleting one or more nucleotides from the 5' end or internal to a promoter); DNA binding protein analysis using DNase I foot printing, methylation interference, electrophoresis mobility-shift assays, in vivo genomic foot printing by ligation-mediated PCR, and other conventional assays; or by DNA sequence comparison with known cis-element motifs using conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation.

(Gene) Expression: Transcription of a DNA molecule into a transcribed RNA molecule. More generally, the processes by which a gene's coded information is converted into the structures present and operating in the cell. Expressed genes include those that are transcribed into mRNA and then translated into protein and those that are transcribed into RNA but not translated into protein (for example, siRNA, transfer RNA and ribosomal RNA). Thus, expression of a target sequence, such as a gene or a promoter region of a gene, can result in the expression of an mRNA, a protein, or both.

The expression of the target sequence can be inhibited or enhanced (decreased or increased). Gene expression may be described as related to temporal, spatial, developmental, or morphological qualities as well as quantitative or qualitative indications.

Gene regulatory activity: The ability of a polynucleotide to affect transcription or translation of an operably linked transcribable or translatable polynucleotide molecule. An isolated polynucleotide molecule having gene regulatory activity may provide temporal or spatial expression or modulate levels and rates of expression of the operably linked transcribable polynucleotide molecule. An isolated polynucleotide molecule having gene regulatory activity may include a promoter, intron, leader, or 3' transcription termination region.

Gene Silencing: Gene silencing refers to lack of (or reduction of) gene expression as a result of, though not limited to, effects at a genomic (DNA) level such as chromatin re-structuring, or at the post-transcriptional level through effects on transcript stability or translation. Current evidence suggests that RNA interference (RNAi) is a major process involved in transcriptional and posttranscriptional gene silencing.

Because RNAi exerts its effects at the transcriptional and/or post-transcriptional level, it is believed that RNAi can be used to specifically inhibit alternative transcripts from the same gene.

Heterologous: A type of sequence that is not normally (e.g., in the wild-type sequence) found adjacent to a second sequence. In one embodiment, the sequence is from a different genetic source, such as a virus or organism or species, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. In RNA molecules, G also will bond to U. Complementary refers to the base pairing that occurs between two distinct nucleic acid sequences or two distinct regions of the same nucleic acid sequence.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

The following is an exemplary set of hybridization conditions and is not meant to be limiting.

Very High Stringency (Detects Sequences that Share 90% Sequence Identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Detects Sequences that Share 80% Sequence Identity or Greater)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Detects Sequences that Share Greater than 50% Sequence Identity)
  Hybridization: 6×SSC at RT to 55° C. for 16-20 hours
  Wash at least twice: 2×-3×SSC at RT to 55° C. for 20-30 minutes each.

In cis: Indicates that two sequences are positioned on the same piece of RNA or DNA.

In trans: Indicates that two sequences are positioned on different pieces of RNA or DNA.

Industrial crop: Crops grown primarily for consumption by humans or animals or for use in industrial processes (for example, as a source of fatty acids for manufacturing or sugars for producing alcohol). It will be understood that in many instances either the plant or a product produced from the plant (for example, sweeteners, oil, flour, or meal) can be consumed; thus, a subset of industrial crops are food crops. Examples of food crops include, but are not limited to, corn, soybean, rice, wheat, oilseed rape, cotton, oats, barley, and potato plants. Other examples of industrial crops (including food crops) are listed herein.

Interfering with or inhibiting (expression of a target sequence): This phrase refers to the ability of a small RNA, such as an siRNA or a miRNA, or other molecule, to measurably reduce the expression and/or stability of molecules carrying the target sequence. A target sequence can include a DNA sequence, such as a gene or the promoter region of a gene, or an RNA sequence, such as an mRNA. "Interfering with or inhibiting" expression contemplates reduction of the end-product of the gene or sequence, e.g., the expression or function of the encoded protein or a protein, nucleic acid, other biomolecule, or biological function influenced by the target sequence, and thus includes reduction in the amount or longevity of the mRNA transcript or other target sequence. In some embodiments, the small RNA or other molecule guides chromatin modifications which inhibit the expression of a target sequence. It is understood that the phrase is relative, and does not require absolute inhibition (suppression) of the sequence. Thus, in certain embodiments, interfering with or inhibiting expression of a target sequence requires that, following application of the small RNA or other molecule (such as a vector or other construct encoding one or more small RNAs), the sequence is expressed at least 5% less than prior to application, at least 10% less, at least 15% less, at least 20% less, at least 25% less, or even more reduced. Thus, in some particular embodiments, application of a small RNA or other molecule reduces expression of the target sequence by about 30%, about 40%, about 50%, about 60%, or more. In specific examples, where the small RNA or other molecule is particularly effective, expression is reduced by 70%, 80%, 85%, 90%, 95%, or even more.

Isolated: An "isolated" biological component (such as a nucleic acid, peptide or protein) has been substantially separated, produced apart from, or purified away from other biological components in the cell of the organism in which the component naturally occurs, e.g., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Metabolome: The complement of relatively low molecular weight molecules (metabolites) that is present in a single organism, a sample, a tissue, a cell, or whatever other division is divided. By way of example, metabolomes may include metabolic intermediates, hormones and other signalling molecules, and secondary metabolites. Representative metabolomes comprise the complement of metabolites found within a biological sample, such as a plant, plant part, or plant sample, or in a suspension or extract thereof. Examples of such molecules include, but are not limited to: acids and related compounds; mono-, di-, and tri-carboxylic acids (saturated, unsaturated, aliphatic and cyclic, aryl, alkaryl); aldo-acids, keto-acids; lactone forms; gibberellins; abscisic acid; alcohols, polyols, derivatives, and related compounds; ethyl alcohol, benzyl alcohol, methanol; propylene glycol, glycerol, phytol; inositol, furfuryl alcohol, menthol; aldehydes, ketones, quinones, derivatives, and related compounds; acetaldehyde, butyraldehyde, benzaldehyde, acrolein, furfural, glyoxal; acetone, butanone; anthraquinone; carbohydrates; mono-, di-, tri-saccharides; alkaloids, amines, and other bases; pyridines (including nicotinic acid, nicotinamide); pyrimidines (including cytidine, thymine); purines (including guanine, adenine, xanthines/hypoxanthines, kinetin); pyrroles; quinolines (including isoquinolines); morphinans, tropanes, cinchonans; nucleotides, oligonucleotides, derivatives, and related compounds; guanosine, cytosine, adeno sine, thymidine, inosine; amino acids, oligopeptides, derivatives, and related compounds; esters; phenols and related compounds; heterocyclic compounds and derivatives; pyrroles, tetrapyrroles (corrinoids and porphines/porphyrins, w/w % metal-ion); flavonoids; indoles; lipids (including fatty acids and triglycerides), derivatives, and related compounds; carotenoids, phytoene; and sterols, isoprenoids including terpenes.

MicroRNA (miRNA): Small, non-coding RNA gene products of approximately 21 nucleotides long and found in diverse organisms, including animals and plants. miRNAs structurally resemble siRNAs except that they arise from structured, foldback-forming precursor transcripts derived from miRNA genes. Primary transcripts of miRNA genes form hairpin structures that are processed by the multidomain RNaseIII-like nuclease DICER and DROSHA (in animals) or DICER-LIKE1 (DCL1; in plants) to yield miRNA duplexes. The mature miRNA is incorporated into RISC complexes after duplex unwinding. Plant miRNAs interact with their RNA targets with perfect or near perfect complementarity.

Nucleotide: The term nucleotide includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in an oligonucleotide/polynucleotide. A nucleotide sequence refers to the sequence of bases in an oligonucleotide/polynucleotide.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Inosine is also a base that can be integrated into DNA or RNA in a nucleotide (dITP or ITP, respectively).

Oil-producing species (of plant): Plant species that produce and store triacylglycerol in specific organs, primarily in seeds. Such species include but are not limited to soybean (*Glycine nizax*), rapeseed and canola (such as *Brassica napus, Brassica rapa* and *Brassica campestris*), sunflower (*Helianthus annus*), cotton (*Gossypium hirsutum*), corn (*Zea mays*), cocoa (*Theobroina cacao*), safflower (*Carthamus tinctorius*), oil palm (*Elaeis guineensis*), coconut palm (*Cocos nucifera*), flax (*Linum usitatissimuin*), castor (*Ricinus commiunis*) and peanut (*Arachis hypogaea*).

Oligonucleotide: An oligonucleotide is a plurality of nucleotides joined by phosphodiester bonds, between about 6 and about 300 nucleotides in length. An oligonucleotide analog refers to compounds that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA Operably linked: This term refers to a juxtaposition of components, particularly nucleotide sequences, such that the normal function of the components can be performed. Thus, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. A coding sequence that is "operably linked" to regulatory sequence(s) refers to a configuration of nucleotide sequences wherein the coding sequence can be expressed under the regulatory control (e.g., transcriptional and/or translational control) of the regulatory sequences.

ORF (open reading frame): A series of nucleotide triplets (codons) coding for amino acids without any termination codons. These sequences are usually translatable into a peptide.

Percent sequence identity: The percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted using tools such as the local homology algorithm of Smith and Waterman, the homology alignment algorithm of Needleman and Wunsch, the search for similarity method of Pearson and Lipman. Such comparisons are preferably carried out using the computerized implementations of these algorithms, such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment (that is, the entire reference sequence or a smaller defined part of the reference sequence). Percent sequence identity is represented as the identity fraction multiplied by 100. The comparison of one or more polynucleotide sequences may be to a full-length polynucleotide sequence or a portion thereof, or to a longer polynucleotide sequence. Substantial percent sequence identity is at least about 80% sequence identity, at least about 90% sequence identity, or even greater sequence identity, such as about 98% or about 99% sequence identity.

Plant: Any plant and progeny thereof. The term also includes parts of plants, including seed, cuttings, tubers, fruit, flowers, etc. In various embodiments, the term plant refers to cultivated plant species, such as corn, cotton, canola, sunflower, soybeans, sorghum, alfalfa, wheat, rice, plants producing fruits and vegetables, and turf and ornamental plant species. The term plant cell, as used herein, refers to the structural and physiological unit of plants, consisting of a protoplast and the surrounding cell wall. The term plant organ, as used herein, refers to a distinct and visibly differentiated part of a plant, such as root, stem, leaf or embryo.

More generally, the term plant tissue refers to any tissue of a plant in planta or in culture. This term includes a whole plant, plant cell, plant organ, protoplast, cell culture, or any group of plant cells organized into a structural and functional unit.

Polynucleotide molecule: Single- or double-stranded DNA or RNA of genomic or synthetic origin; that is, a polymer of deoxyribonucleotide or ribonucleotide bases, respectively, read from the 5' (upstream) end to the 3' (downstream) end.

Polypeptide molecule: A polymer in which the monomers are amino acid residues which are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

Post-Transcriptional Gene Silencing (PTGS): A form of gene silencing in which the inhibitory mechanism occurs after transcription. This can result in either decreased steady-state level of a specific RNA target or inhibition of translation (Tuschl, ChemBiochem, 2: 239-245, 2001). In the literature, the terms RNA interference (RNAi) and posttranscriptional cosuppression are often used to indicate posttranscriptional gene silencing.

Promoter: An array of nucleic acid control sequences which direct transcription of a nucleic acid, by recognition and binding of e.g., RNA polymerase II and other proteins (trans-acting transcription factors) to initiate transcription. A promoter includes necessary nucleic acid sequences near the start site of transcription, such as, in the case of a polymerase II type promoter, a TATA element. Minimally, a promoter typically includes at least an RNA polymerase binding site together and may also include one or more transcription factor binding sites which modulate transcription in response to occupation by transcription factors. Representative examples of promoters (and elements that can be assembled to produce a promoter) are described herein. Promoters may be defined by their temporal, spatial, or developmental expression pattern.

A plant promoter is a native or non-native promoter that is functional in plant cells.

Protein: A biological molecule, for example a polypeptide, expressed by a gene and comprised of amino acids.

Protoplast: An isolated plant cell without a cell wall, having the potential for being transformed and/or regeneration into cell culture or a whole plant.

Purified: The term purified does not require absolute purity; rather, it is intended as a relative term. Thus, for example, a purified fusion protein preparation is one in which the fusion protein is more enriched than the protein is in its generative environment, for instance within a cell or in a biochemical reaction chamber. Preferably, a preparation of fusion protein is purified such that the fusion protein represents at least 50% of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Similarly, a recombinant protein is one encoded for by a recombinant nucleic acid molecule.

Regulatable promoter: A promoter the activity of which is regulated (directly or indirectly) by an agent, such as a transcription factor, a chemical compound, an environmental condition, or a nucleic acid molecule.

Regulating gene expression: Processes of controlling the expression of a gene by increasing or decreasing the expression, production, or activity of an agent that affects gene expression. The agent can be a protein, such as a transcription factor, or a nucleic acid molecule, such as a miRNA or an siRNA molecule, which when in contact with the gene or its upstream regulatory sequences, or a mRNA encoded by the gene, either increases or decreases gene expression.

Regulatory sequences or elements: These terms refer generally to a class of polynucleotide molecules (such as DNA molecules, having DNA sequences) that influence or control transcription or translation of an operably linked transcribable polynucleotide molecule, and thereby expression of genes. Included in the term are promoters, enhancers, leaders, introns, locus control regions, boundary elements/insulators, silencers, Matrix attachment regions (also referred to as scaffold attachment regions), repressor, transcriptional terminators (a.k.a. transcription termination regions), origins of replication, centromeres, and meiotic recombination hotspots. Promoters are sequences of DNA near the 5' end of a gene that act as a binding site for RNA polymerase, and from which transcription is initiated. Enhancers are control elements that elevate the level of transcription from a promoter, usually independently of the enhancer's orientation or distance from the promoter. Locus control regions (LCRs) confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also known as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. Matrix attachment regions (MARs), also known as scaffold attachment regions, are sequences within DNA that bind to the nuclear scaffold. They can affect transcription, possibly by separating chromosomes into regulatory domains. It is believed that MARs mediate higher-order, looped structures within chromosomes. Transcriptional terminators are regions within the gene vicinity that RNA polymerase is released from the template. Origins of replication are regions of the genome that, during DNA synthesis or replication phases of cell division, begin the replication process of DNA. Meiotic recombination hotspots are regions of the genome that recombine more frequently than the average during meiosis. Specific nucleotides within a regulatory region may serve multiple functions. For example, a specific nucleotide may be part of a promoter and participate in the binding of a transcriptional activator protein.

Isolated regulatory elements that function in cells (for instance, in plants or plant cells) are useful for modifying plant phenotypes, for instance through genetic engineering.

RNA: A typically linear polymer of ribonucleic acid monomers, linked by phosphodiester bonds. Naturally occurring RNA molecules fall into three general classes, messenger (mRNA, which encodes proteins), ribosomal (rRNA, components of ribosomes), and transfer (tRNA, molecules responsible for transferring amino acid monomers to the ribosome during protein synthesis). Messenger RNA includes heteronuclear (hnRNA) and membrane-associated polysomal RNA (attached to the rough endoplasmic reticulum). Total RNA refers to a heterogeneous mixture of all types of RNA molecules.

RNA interference (RNAi): Gene silencing mechanisms that involve small RNAs (including miRNA and siRNA) are frequently referred to under the broad term RNAi. Natural functions of RNAi include protection of the genome against invasion by mobile genetic elements such as transposons and viruses, and regulation of gene expression.

RNA interference results in the inactivation or suppression of expression of a gene within an organism. RNAi can be triggered by one of two general routes. First, it can be triggered by direct cellular delivery of short-interfering RNAs (siRNAs, usually ~21 nucleotides in length and delivered in a dsRNA duplex form with two unpaired nucleotides at each 3' end), which have sequence complementarity to a RNA that is the target for suppression. Second, RNAi can be triggered by one of several methods in which siRNAs are formed in vivo from various types of designed, expressed genes. These genes typically express RNA molecules that form intra- or intermolecular duplexes (dsRNA) which are processed by natural enzymes (DICER or DCL) to form siRNAs. In some cases, these genes express "hairpin"-forming RNA transcripts with perfect or near-perfect base-pairing; some of the imperfect hairpin-forming transcripts yield a special type of small RNA, termed microRNA (miRNA). In either general method, it is the siRNAs (or miRNAs) that function as "guide sequences" to direct an RNA-degrading enzyme (termed RISC) to cleave or silence the target RNA. In some cases, it is beneficial to integrate an RNAi-inducing gene into the genome of a transgenic organism. An example would be a plant that is modified to suppress a specific gene by an RNAi-inducing transgene. In most methods that are currently in practice, RNAi is triggered in transgenic plants by transgenes that express a dsRNA (either intramolecular or hairpin, or intermolecular in which two transcripts anneal to form dsRNA).

RNA silencing: A general term that is used to indicate RNA-based gene silencing or RNAi.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the sequences referenced or disclosed herein, such as homologs of the SCBV enhancer element, will possess a relatively high degree of sequence identity when aligned using standard methods.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS USA* 85: 2444, 1988); Higgins and Sharp (*Gene,* 73: 237-244, 1988); Higgins and Sharp (*CABIOS* 5: 151-153, 1989); Corpet et al. (*Nuc. Acids Res.* 16: 10881-90, 1988); Huang et al. (*Comp. Appls Biosci.* 8: 155-65, 1992); and Pearson et al. (*Methods in Molecular Biology* 24: 307-31, 1994). Altschul et al. (*Nature Genet.,* 6: 119-29, 1994) presents a detailed consideration of sequence alignment methods and homology calculations.

The alignment tools ALIGN (Myers and Miller, *CABIOS* 4: 11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at biology.ncsa.uiuc.edu.

Orthologs or paralogs (more generally, homologs) of the disclosed sequences are typically characterized by possession of greater than 75% sequence identity counted over the full-length alignment with the sequence to which they are compared using ALIGN set to default parameters. Sequences with even greater similarity to the reference sequences will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins. In such an instance, percentage identities will be essentially similar to those discussed for full-length sequence identity.

When significantly less than the entire sequence is being compared for sequence identity, homologs will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods can be found at World Wide Web address biology.ncsa.uiuc.edu. One of skill in the art will appreciate that these sequence identity ranges are provided for guidance only; it is entirely possible that strongly significant homologs could be obtained that fall outside of the ranges provided. The present disclosure provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology* Part I, Ch. 2, Elsevier, N.Y., 1993). Nucleic acid molecules that hybridize under stringent conditions to the disclosed SCBV enhancer sequences will typically hybridize to a probe based on either the entire fusion protein encoding sequence, an entire binding domain, or other selected portions of the encoding sequence under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Small interfering RNA (siRNA): RNA of approximately 21-25 nucleotides that is processed from a dsRNA by a DICER enzyme (in animals) or a DCL enzyme (in plants). The initial DICER or DCL products are double-stranded, in which the two strands are typically 21-25 nucleotides in length and contain two unpaired bases at each 3' end. The individual strands within the double stranded siRNA structure are separated, and typically one of the siRNAs then are associated with a multi-subunit complex, the RNAi-induced silencing complex (RISC). A typical function of the siRNA is to guide RISC to the target based on base-pair complementarity.

Transcribable polynucleotide molecule: Any polynucleotide molecule capable of being transcribed into a RNA molecule. Methods are known to those of ordinary skill, for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. Conventional compositions and methods for preparing and using constructs and host cells are well known to one skilled in the art (see for example, *Molecular Cloning: A Laboratory Manual*, 3rd edition Volumes 1, 2, and 3. Sambrook et al., Cold Spring Harbor Laboratory Press, 2000).

Transcription: The production of an RNA molecule by RNA polymerase as a complementary copy of a DNA sequence.

Transcription termination region: Sequences that control formation of the 3' end of a transcript. Self-cleaving ribozymes and polyadenylation sequences are examples of transcription termination sequences.

Transcriptional gene silencing (TGS): A phenomenon that is triggered by the formation of dsRNA that is homologous with gene promoter regions and sometimes coding regions. TGS results in DNA and histone methylation and chromatin remodeling, thereby causing transcriptional inhibition rather than RNA degradation. Both TGS and PTGS depend on dsRNA, which is cleaved into small (21-25 nucleotides) interfering RNAs (Eckhardt, *Plant Cell,* 14:1433-1436, 2002; Aufsatz et al., *Proc. Natl. Acad. Sci. U.S.A.,* 99:16499-16506, 2002).

Transgenic: This term refers to a plant/fungus/cell/other entity or organism that contains recombinant genetic material not normally found in entities of this type/species (that is, heterologous genetic material) and which has been introduced into the entity in question (or into progenitors of the entity) by human manipulation. Thus, a plant that is grown from a plant cell into which recombinant DNA is introduced by transformation (a transformed plant cell) is a transgenic plant, as are all offspring of that plant that contain the introduced transgene (whether produced sexually or asexually).

Transformation: Process by which exogenous DNA enters and changes a recipient cell. It may occur under natural conditions, or artificial conditions using various methods well known in the art. Transformation may rely on any known method for the insertion of foreign nucleic acid sequences into a prokaryotic or eukaryotic host cell. Selection of the method is influenced by the host cell being transformed and may include, but is not limited to, viral infection, electroporation, lipofection, and particle bombardment.

Transformed: A transformed cell is a cell into which has been introduced a nucleic acid molecule by molecular biology techniques. Transformed cells include stably transformed cells in which the inserted DNA is capable of replication either as an autonomously replicating plasmid or as part of the host chromosome. They also include cells that transiently express the inserted DNA or RNA for limited periods of time. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transposon: A nucleotide sequence such as a DNA or RNA sequence that is capable of transferring location or moving within a gene, a chromosome or a genome.

Transgenic plant: A plant that contains a foreign (heterologous) nucleotide sequence inserted into either its nuclear genome or organellar genome.

Transgene: A nucleic acid sequence that is inserted into a host cell or host cells by a transformation technique.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

The present disclosure describes novel transcription initiation regions comprising an enhancer domain and, under the enhancing control of the enhancer domain, a transcription regulatory domain. The enhancer domain comprises a plurality (e.g., two to four or more) of copies of a natural but previously unrecognized SCBV enhancer arranged in tandem. The transcription regulatory regions (promoters) of the present disclosure provide enhanced transcription as compared to the promoter in the absence of the enhancer domain.

In one embodiment, a chimeric transcription regulatory region is disclosed comprising one or more copies of the SCBV enhancer element shown in position 337 to position 618 of SEQ ID NO: 1 (or a homolog thereof); and operably linked thereto, a promoter comprising an RNA polymerase binding site and a mRNA initiation site, wherein when a nucleotide sequence of interest is transcribed under regulatory control of the chimeric transcription regulatory region, the amount of transcription product is enhanced compared to the amount of transcription product obtained with the chimeric transcription regulatory region comprising the promoter and not comprising the SCBV enhancer sequence(s). In some embodiments, the chimeric transcription regulatory region comprises a promoter obtained from the upstream region of a plant virus gene, a bacterial gene, a fungal gene, a plant nuclear gene, a plant extra-nuclear gene, an invertebrate gene, or a vertebrate gene.

Also provided are DNA constructs comprising a described transcription regulatory region and a DNA sequence to be transcribed. In some embodiments, a DNA construct is disclosed comprising the transcriptional initiation region operably linked to a transcribable polynucleotide molecule operably linked to a 3' transcription termination polynucleotide molecule. In one embodiment, the transcribable polynucleotide molecule confers an agronomic trait to a plant in which it is expressed.

Also provided are transgenic plants. In one embodiment, a transgenic plant is stably transformed with a disclosed DNA construct. In some embodiments, the transgenic plant is a dicotyledon. In other embodiments, the transgenic plant is a monocotyledon. In one particular embodiment, the transgenic plant is a maize plant.

Further provided is a seed of a disclosed transgenic plant. In one embodiment, the seed comprises the disclosed DNA construct.

Even further provided is a transgenic plant cell or tissue. In one embodiment, a transgenic plant cell or tissue comprises a disclosed chimeric transcription regulatory region. In some embodiments, the plant cell or tissue is derived from a dicotyledon. In other embodiments, the plant cell or tissue is from a monocotyledon. In one particular embodiment, the plant cell or tissue is from a maize plant.

Also provided are methods of producing a disclosed transgenic plant, plant cell, seed or tissue. In some embodiments, the method comprises transforming a plant cell or tissue with a disclosed DNA construct.

Further provided are a plant cell, fruit, leaf, root, shoot, flower, seed, cutting and other reproductive material useful in sexual or asexual propagation, progeny plants inclusive of F1 hybrids, male-sterile plants and all other plants and plant products derivable from the disclosed transgenic plants.

Also disclosed is a maize plant cell, tissue or plant comprising one or more copies of a SCBV enhancer element shown in position 337 to position 618 of SEQ ID NO: 1. In one embodiment, a maize plant cell, tissue or plant comprises one or more copies of a SCBV enhancer element shown in position 337 to position 618 of SEQ ID NO: 1 in which the one or more copies of the SCBV enhancer element is inserted into a genome of the maize plant cell, tissue or plant at a random location. In some embodiments, the SCBV enhancer imparts enhanced transcription of a nucleotide sequence of interest which is under regulatory control of the SCBV enhancer as compared to transcription of the nucleotide sequence of interest in the absence of the SCBV enhancer.

IV. SCBV Enhancer and Its Uses

The present disclosure provides a previously unrecognized enhancer region from the Sugarcane Bacilliform badnavirus (SCBV) genome, which enhancer is useful in enhancing the transcription efficiency which may result in enhanced transcription of DNA sequences under control of the enhancer. Of particular interest is enhanced transcription of gene sequences which may be of the same genetic origin as the host or of foreign origin, either the naturally occurring sequences (in both sense and antisense orientations) or synthetically prepared sequences. The subject enhancers comprise a plurality of two or more copies of a previously unrecognized natural SCBV enhancer domain (the sequence of which is provided in SEQ ID NO: 1, at positions 337 to 618). The enhancer comprises at least two copies of the enhancer domain sequence, in some embodiments three or four or more copies, arranged in tandem.

Also contemplated are homologous enhancers. Without intending to be limited in any way, representative homologous sequences may include those from other SCBV promoters, for instance from different SCBV isolates such as those described in Braithwaite et al. (*Plant Cell Rep.* 23:319-326, 2004; incorporated herein by reference in its entirety) or in U.S. Pat. No. 5,994,123 (incorporated herein by reference in its entirety).

A natural enhancer comprises a DNA sequence which in its native environment is upstream from and within about 600 by of a promoter. Taking the initial nucleotide of the mRNA as 0, the sequence containing an enhancer is from about −50 to about −1,000 bp, usually from about −50 to −950 bp, generally comprising about −100 to −800 bp. An enhancer domain is cis-acting and desirably is located within about 10,000 bp, usually about 2,000 bp, more usually adjacent to or within about 1,000 by of a transcription initiation sequence to be enhanced. The enhancer may be in either orientation with respect to the transcription initiation sequence and can be located upstream or downstream in relation to the promoter it enhances, though it is usually upstream.

The enhancer domain of the present disclosure finds use with a wide variety of initiation sequences, including promoters that are naturally found under the control of the enhancer, e.g., in a cis position (adjacent and homologous) as well as those not normally associated with the particular enhancer (e.g., heterologous). The enhancer domain and transcription initiation domain may be from the same or different kingdom, family or species. Species of interest include prokaryotes and eukaryotes, such as bacteria, plants, insects, mammals, etc. Combinations include the described SCBV (viral) enhancer domain(s) with a transcription initiation region of a structural gene of: a host for SCBV (e.g., from sugarcane), another plant species (e.g., of the same or a different family), an insect, a vertebrate animal, a bacterium, a fungus, and so forth.

The disclosure also contemplates DNA constructs comprising a subject transcription initiation region and, under the control of the transcription initiation region, a DNA sequence to be transcribed. The DNA sequence may comprise a natural open reading frame including transcribed 5' and 3' flanking sequences. Alternatively, it may comprise an anti-sense sequence in that it encodes the complement of an RNA molecule or portion thereof. When the construct includes an open reading frame (ORF) which encodes a protein, an enhanced transcription initiation rate is obtained, usually providing an increased amount of the polypeptide expression product of the gene. When the construct comprises an anti-sense sequence, the enhanced transcription of RNA complementary to wild type suppresses the expression of the wild type mRNA, thereby decreasing the amount of the polypeptide expression product; it is contemplated that the wild type mRNA in question may correspond to a native mRNA of the host cell or a mRNA of a pathogen, such as a virus or fungus.

In various embodiments, the DNA sequence to be transcribed includes: protein encoding sequence(s) of a gene (e.g., from a plant, animal, bacterium, virus, or fungus), which may include: natural open reading frame(s) encoding a protein product; complementary DNA (cDNA) sequences derived from mRNA encoded by a gene; synthetic DNA giving the desired coding sequence(s); protein encoding sequence(s) derived from exons of a natural gene, such as open reading frame(s) produced by exon ligation; and/or combinations of any two or more thereof. Attached to these sequences are appropriate transcription termination/polyadenylation sequences; sequences from a natural gene (e.g., from a plant, animal, bacterium, virus, or fungus) that encodes a primary RNA product, that is consisting of exons and introns (e.g., natural Polymerase II and Polymerase III transcribed genes of eukaryotes); synthetic DNA sequences that encode a specific RNA or protein product; sequences of DNA modified from a known coding sequence (e.g., a natural gene sequence) by mutagenesis (such as site specific mutagenesis) and/or other genetic engineering technology; chimeras of any of the above achieved by ligation of DNA fragments, including chimeras that encode fusion proteins; and/or DNA sequences encoding the complement of RNA molecules or portions thereof.

Enhanced transcription in plants may find use in enhancing the production of proteins characteristic of the plant (endogenous—that is, normally found in the wild-type host) or those proteins from other genetic sources (exogenous—that is, not normally found in the wild-type host). Examples of types of sequences to be expressed from the enhancers and chimeric transcription regulatory regions described herein include: antisense or small inhibitory RNAs (for gene suppression); nutritionally important proteins; growth promoting factors; proteins giving protection to the plant under certain environmental conditions, e.g., proteins conferring resistance to metal, salt, or other toxicity; stress related proteins giving tolerance to extremes of temperature, freezing, etc.; proteins conferring pest or infection-related protection to the plant, e.g., proteins giving resistance to bacterial, fungal, or other microbial infection, or resistance to predation by insects (e.g., *B. thuringiensis* toxin) or to other invertebrate or vertebrate animals; compounds of medical importance outside of the plant, e.g., anti-microbial, anti-tumor, etc.; proteins or other compounds of specific commercial value; increased level of proteins, e.g., enzymes of metabolic pathways (e.g., pathways for production of polyphenolic compounds or other secondary metabolites); increased levels of products of structural value to a plant host; and so forth. The sequences of interest which are transcribed will be of at least about 8 bp, at least about 12 bp, at least about 20 bp, and may be one or more kilobase pairs (kbp) in length.

V. Constructs

Constructs of the present disclosure typically contain a chimeric transcription regulatory region comprising one or more copies of the provided SCBV enhancer element operably linked to a promoter (usually containing at least an RNA polymerase binding site and a mRNA initiation site), which region is operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5'-untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see for example, U.S. Pat. Nos. 5,659,122 and 5,362,865 each of which is incorporated by reference in its entirety). Such additional upstream and downstream regulatory polynucleotide molecules as are present in the construct may be derived from a source that is native or heterologous with respect to the other elements present on the construct.

Thus, one embodiment is a construct comprising a chimeric transcription regulatory region itself comprising one or more copies (e.g., two, three, four or more copies) of the SCBV enhancer element shown in position 337 to position 618 of SEQ ID NO: 1 (or a homolog thereof) operably linked to a promoter, operably linked to a transcribable polynucleotide molecule so as to direct transcription of said transcribable polynucleotide molecule at a desired level and/or in a desired tissue or developmental pattern upon introduction of the construct into a plant cell. The transcribable polynucleotide molecule in some examples comprises a protein-coding region of a gene, and the chimeric transcription regulatory region provides transcription of a functional mRNA molecule that is translated and expressed as a protein product from the construct. In another embodiment, the transcribable polynucleotide molecule comprises an antisense region of a gene, and the chimeric transcription regulatory region affects transcription of an antisense RNA molecule or other similar inhibitory RNA in order to inhibit expression of a specific RNA molecule of interest in a target host cell.

Yet more example constructs of the present disclosure include double Ti plasmid border DNA constructs that have the right border (RB or AGRtu.RB) and left border (LB or AGRtu.LB) regions of the Ti plasmid isolated from *Agrobacterium tumefaciens* comprising a T-DNA, which along with transfer molecules provided by the *Agrobacterium* cells, enable integration of the T-DNA into the genome of a plant cell. The constructs may also contain plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, representative host bacterial strains include *Agrobacterium tumefaciens* ABI, C58, or LBA4404; however, other strains known to those skilled in the art of plant transformation can be used.

Also contemplated are constructs comprising at least one SCBV enhancer element (optionally in the context of a chimeric transcription regulatory region), which construct is an activation tagging construct. Activation tagging is a method by which genes are randomly and strongly upregulated on a genome-wide scale, after which specific phenotypes can be screened for and selected. Components useful in various types of activating tagging constructs are known; see, for instance: Walden et al., *Plant Mol. Biol.* 26: 1521-8, 1994 (describing an activation T-DNA tagging construct that was used to activate genes in tobacco cell culture allowing the cells to grow in the absence of plant growth hormones); Miklashevichs et al., *Plant J.* 12: 489-98, 1997; Harling et al., *EMBO J.* 16: 5855-66, 1997; Walden et al., *EMBO J.* 13: 4729-36, 1994 (reports of genes isolated from plant genomic sequences flanking the T-DNA tag and putatively involved in plant growth hormone responses); Schell et al., *Trends Plant Sci.* 3: 130, 1998 (discussing investigation of a group of related studies); Kardailsky et al., *Science* 286: 1962-1965, 1999 (describing activation T-DNA tagging and screening of plants for an early flowering phenotype); Koncz et al., *Proc Natl Acad Sci USA* 86(21):8467-71, 1989 (describing activation tagging using the *Agrobacterium* gene 5 promoter (pg5), which is active only in proliferating cells and must insert directly adjacent to a plant gene in order to influence its expression); Wilson et al., *Plant Cell* 8: 659-671, 1996 (activation tagging that utilizes a modified Ds transposon carrying the CaMV 35S promoter and a nos::hpt selection cassette) and Schaffer et al., *Cell* 93: 1219-1229, 1998 (illustrating the same system, used to upregulate adjacent plant genes resulting in dominant gain-of-function mutations 1996); and Weigel et al., *Plant Physiology*, 122:1003-1013, 2000 (illustrating activation tagging vectors that are useful for screening tens of thousands of transformed plants for morphological phenotypes).

VI. Nucleotide Sequences for Transcription Enhancement

Exemplary transcribable polynucleotide molecules for transcription enhancement by incorporation into constructs as provided herein include, for example, polynucleotide molecules or genes from a species other than the target species or genes that originate with or are present in the same species, but are incorporated into recipient cells by genetic engineering methods rather than classical reproduction or breeding techniques. The type of polynucleotide molecule can include but is not limited to a polynucleotide molecule that is already present in the target plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

In one embodiment, a polynucleotide molecule as shown in positions 337 to 618 of SEQ ID NO: 1 (or two or more copies thereof) (for instance, in the context of a chimeric transcription initiation region) is incorporated into a construct such that the described SCBV enhancer sequence (or series of two or more such sequences) is operably linked to a transcribable polynucleotide molecule that is a gene of agronomic interest or other expression sequence (more generally, a nucleotide sequence of interest). As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait, for instance. A gene of agronomic interest that provides a beneficial agronomic trait to crop plants may be, for example, one or more sequences conferring to a plant expressing the gene: herbicide resistance (see, e.g., U.S. Pat. Nos. 6,803,501; 6,448,476; 6,248,876; 6,225,114; 6,107,549; 5,866,775; 5,804,425; 5,633,435; 5,463,175; and U.S. Publications US20030135879 and US20030115626), increased yield (see, e.g., U.S. Pat. RE38,446; U.S. Pat. Nos. 6,716,474; 6,663,906; 6,476,295; 6,441,277; 6,423,828; 6,399,330; 6,372,211; 6,235,971; 6,222,098; 5,716,837), insect control (see, e.g., U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; 5,763,241), fungal disease resistance (see, e.g., U.S. Pat. Nos. 6,653,280; 6,573,361; 6,506,962; 6,316,407; 6,215,048; 5,516,671; 5,773,696; 6,121,436; 6,316,407; 6,506,962), virus resistance (see, e.g., U.S. Pat. Nos. 6,617,496; 6,608,241; 6,015,940; 6,013,864; 5,850,023; 5,304,730), nematode resistance (see, e.g., U.S. Pat. No. 6,228,992), bacterial disease resistance (see, e.g., U.S. Pat. No. 5,516,671), plant growth and development (see, e.g., U.S. Pat. Nos. 6,723,897; 6,518,488), starch production (see, e.g., U.S. Pat. Nos. 6,538,181; 6,538,179; 6,538,178; 5,750,876; 6,476,295), modified oils production (see, e.g., U.S. Pat. Nos. 6,444,876; 6,426,447; 6,380,462), high oil production (see, e.g., U.S. Pat. Nos. 6,495,739; 5,608,149; 6,483,008; 6,476, 295), modified fatty acid content (see, e.g., U.S. Pat. Nos. 6,828,475; 6,822,141; 6,770,465; 6,706,950; 6,660,849; 6,596,538; 6,589,767; 6,537,750; 6,489,461; 6,459,018), fiber production (see, e.g., U.S. Pat. Nos. 6,576,818; 6,271, 443; 5,981,834; 5,869,720), high protein production (see, e.g., U.S. Pat. No. 6,380,466), fruit ripening (see, e.g., U.S. Pat. No. 5,512,466), improved digestibility (see, e.g., U.S. Pat. No. 6,531,648), improved flavor (see, e.g., U.S. Pat. No. 6,011,199), low raffinose (see, e.g., U.S. Pat. No. 6,166,292), enhanced animal and/or human nutrition (see, e.g., U.S. Pat. Nos. 6,723,837; 6,653,530; 6,541,259; 5,985,605; 6,171,640), environmental stress resistance (see, e.g., U.S. Pat. No. 6,072,103), desirable peptides (e.g., pharmaceutical or secretable peptides) (see, e.g., U.S. Pat. Nos. 6,812,379; 6,774,283; 6,140,075; 6,080,560), improved processing traits (see, e.g., U.S. Pat. No. 6,476,295), industrial enzyme production (see, e.g., U.S. Pat. No. 5,543,576), nitrogen fixation (see, e.g., U.S. Pat. No. 5,229,114), hybrid seed production (see, e.g., U.S. Pat. No. 5,689,041), biopolymers (see, e.g., U.S. Pat. No. RE37,543; U.S. Pat. Nos. 6,228,623; 5,958,745 and U.S. Publication No. US20030028917) and biofuel production (see, e.g., U.S. Pat. No. 5,998,700). The genetic elements, methods, and transgenes described in the patents and published applications listed above are incorporated herein by reference.

Alternatively, a transcribable polynucleotide molecule can influence an above mentioned (or other) plant characteristic or phenotypes by encoding an antisense or RNA molecule that causes the targeted inhibition of expression of an endogenous gene, for example via antisense, inhibitory RNA (RNAi), or cosuppression-mediated mechanisms. The RNA could also be a catalytic RNA molecule (a ribozyme) engineered to cleave a desired endogenous mRNA product. Thus, any transcribable polynucleotide molecule that encodes a transcribed RNA molecule that affects a phenotype, biochemical or morphological change of interest may benefit from the transcriptional enhancement enabled by the sequences and constructs provided herein.

The described SCBV enhancer or chimeric transcription regulatory region comprising one or more copies thereof can be incorporated into a construct with one or more marker genes (any transcribable polynucleotide molecule whose expression can be screened for or scored in some way) and tested in transient or stable plant analyses to provide an indication of the regulatory element's gene expression pattern in stable transgenic plants. Marker genes for use in the practice of such embodiments include, but are not limited to transcribable polynucleotide molecules encoding β-glucuronidase (GUS described in U.S. Pat. No. 5,599,670) and green fluorescent protein (GFP described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS described in U.S. Pat. Nos. 5,627,061, 5,633,435, 6,040,497 and in U.S. Pat. No. 5,094,945 for glyphosate tolerance); polynucleotides encoding a glyphosate oxidoreductase and a glyphosate-N-acetyl transferase (GOX described in U.S. Pat. No. 5,463,175 and GAT described in U.S. publication No. 20030083480); a polynucleotide molecule encoding bromoxynil nitrilase (Bxn described in U.S. Pat. No. 4,810,648 for Bromoxynil tolerance); a polynucleotide molecule encoding phytoene desaturase (crtI) described in Misawa et al. (*Plant J.* 4:833-840, 1993) and Misawa et al. (*Plant J.* 6:481-489, 1994) for norflurazon tolerance; a polynucleotide molecule encoding acetohydroxyacid synthase (AHAS, aka ALS) described in Sathasiivan et al. (*Nucl. Acids Res.* 18:2188-2193, 1990) for tolerance to sulfonylurea herbicides; a polynucleotide molecule encoding a dicamba-degrading oxygenase enzyme (described in U.S. Patent Publications US20030135879 and US20030115626, for dicamba tolerance); and the bar gene described in DeBlock et al. (*EMBO J.* 6:2513-2519, 1987) for glufosinate and bialaphos tolerance. The regulatory elements of the present disclosure can express transcribable polynucleotide molecules that encode phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Constructs containing at least one SCBV enhancer (for instance, in the context of a chimeric transcription regulatory region) operably linked to a marker gene or other nucleotide sequence of interest may be delivered to a tissues (e.g., transformed) and the tissues analyzed by the appropriate mechanism, depending on the marker or sequence that is being transcribed. Such quantitative or qualitative analyses may be used as tools to evaluate the potential expression profile of a regulatory element when operatively linked to a gene of agronomic interest in stable plants. Marker gene can be used in a transient assay; methods of testing for marker gene expression in transient assays are known to those of ordinary skill in the art. Transient expression of marker genes has been reported using a variety of plants, tissues, and DNA delivery systems. For example, transient analyses systems include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present disclosure encompasses use of any transient expression system to evaluate regulatory elements operably linked to any transcribable polynucleotide molecule, including but not limited to marker genes or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

VII. Plant Transformation

A plant transformation construct containing an enhancer element (or multiple copies thereof) or a chimeric transcription regulatory region such as is described herein may be introduced into plants using any plant transformation method. Methods and materials for transforming plants by introducing a plant expression construct into a plant genome in the practice of this invention can include any of the well-known and demonstrated methods including electroporation (e.g., U.S. Pat. No. 5,384,253), microprojectile bombardment (e.g., U.S. Pat. Nos. 5,015,580; 5,550,318; 5,538,880; 6,160,208; 6,399,861; and 6,403,865), *Agrobacterium*-mediated transformation (e.g., U.S. Pat. Nos. 5,824,877; 5,591,616; 5,981,840; and 6,384,301), and protoplast transformation (e.g., U.S. Pat. No. 5,508,184). It will be apparent to those of skill in the art that a number of transformation methodologies can be used and modified for production of stable transgenic plants from any number of target crops of interest.

Specific methods for transforming dicots are known to those skilled in the art. By way of example, transformation and plant regeneration methods have been described for a number of crops including, but not limited to, cotton (*Gossypium hirsutum*), soybean (*Glycine max*), peanut (*Arachis hypogaea*), and members of the genus *Brassica*.

Likewise, specific methods for transforming monocots are also known to those skilled in the art. By way of example transformation and plant regeneration methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. *Agrostis stolonifera, Poa pratensis, Stenotaphrum secundatum*); wheat (*Triticum aestivum*), and alfalfa (*Medicago sativa*).

The transformed plants may be analyzed for the presence of the gene(s) of interest and the expression level and/or profile conferred by the chimeric transcription regulatory regions described herein. Numerous methods are available to those of ordinary skill in the art for the analysis of transformed plants. For example, methods for plant analysis include Southern and northern blot analysis, PCR-based (or other nucleic acid amplification-based) approaches, biochemical analyses, phenotypic screening methods, field evaluations, and immunodiagnostic assays (e.g., for the detection, localization, and/or quantification of proteins).

Enhanced expression of genes using the described SCBV enhancer has been demonstrated in maize, but the enhancer is expected to function in other plant species, possibly including dicots as well as monocots. The enhancer element with four copies of the SCBV upstream region provided the highest level of expression of the combinations studied herein. Fewer or more copies of the upstream region, as well as, combinations with enhancer elements from other sources could also provide advantages for modulating gene expression. The same activators, constructs and approaches may be useful for other crop species for which genes may be identified because genome sequence is available or in progress (including *Sorghum* (*Sorghum bicolor*), Wheat (*Triticum aestivum*), Barley (*Hordeum vulgare*), Foxtail millet (*Setaria italica*), Sugarcane (*Saccharum officinarum*), *Miscanthus giganteus* or for which 'activated genes' may be identified by future genome sequencing efforts or perhaps chromosomal synteny (including Oats (*Avena sativa*), Rye (*Secale cereale*), Pearl millet (*Pennisetum glaucum*), Finger millet (*Eluesine coracana*), Proso millet (*Panicum miliaceum*), Teff millet (*Eragrostis tef*)), or for model grass species for which genomic sequence is available or in progress (including Purple False Brome (*Brachypodium distachyon*), Green bristlegrass (*Setaria viridis*)).

The following examples are provided to illustrate certain particular features and/or embodiments. These examples should not be construed to limit the invention to the particular features or embodiments described.

Example 1

Identification of Sequences Comprising Enhancer Element of Sugarcane Baciliform Virus (SCBV) Promoter This example demonstrates the identification of sequences including the SCBV promoter enhancer element.

A promoter fragment derived from the genome of a SCBV (GenBank Accession No. AJ277091, and described by Geijskes et al., *Arch. Virol.*, 147: 2393-2404, 2002) was first examined by transient expression assays to determine which regions of the promoter sequence contain enhancer element sequences. In the promoter analysis study, fragments derived from the SCBV promoter (SEQ ID NO: 1) containing sequences from −839 to +106 by (plasmid pSCBV839), from −576 to +106 by (plasmid pSCBV576), and from −333 to +106 by (plasmid pSCBV333) from the transcription start site (defined as the +1 position) were cloned upstream of a coding region for a firefly luciferase (LUC) reporter protein. Transcription was terminated by a copy of the nopaline synthase (Nos) 3' UTR region (as disclosed in bases 1847 to 2103 of GenBank Accession No. V00087.1, which is hereby incorporated by reference in its entirety; and FIG. 1). Transient transcriptional activities of these constructs were tested by transforming them by particle bombardment into maize Hi-II suspension cells (described in detail in Example 2 below) and monitoring activity of the LUC reporter gene. Luciferase activity was normalized in each experiment by co-transforming with a equimolar amount of the plasmid DNA containing an SCBV:LUC construct and DNA of a reference plasmid harboring a construct consisting of a maize ubiquitin 1 (ubi1) gene promoter (as disclosed in U.S. Pat. No. 5,510,474 which is hereby incorporated by reference in its entirety; essentially bases 7 to 1990 of GenBank Accession No. S94464.1, which is hereby incorporated by reference in its entirety) driving expression of a GUS (beta-glucuronidase) coding region, and terminated by a maize PerS 3' UTR terminator (as disclosed in U.S. Pat. No. 6,699,984, which is hereby incorporated by reference in its entirety; e.g., construct ubi1:GUS). Two days after bombardment, total protein was isolated from transformed cells and LUC enzymatic activity (expressed in Luciferase Units (LU)/mg protein) and GUS enzymatic activity (expressed in GUS activity units (GU)/µg protein) were measured by methods found in, for example, (Maliga et al., *Methods in Plant Molecular Biology. A Laboratory Course Manual*. Cold Spring Harbor Laboratory Press, 1995). Relative activities of the test promoters in the three SCBV:LUC constructs were compared by normalizing LUC levels to GUS levels as the ratio of LU/mg protein:GU/μg protein. The transient testing results showed that LUC activity increased linearly with increasing concentrations of plasmid DNA bombarded, indicating that LUC activity is correlated with transcript levels. Further, the SCBV promoter fragment containing sequences from −576 bp upstream to +106 downstream of the transcription start site had 66%±2% of the activity of the full-length promoter fragment (here defined as containing the sequences from −839 bp upstream to +106 downstream of the start site). In contrast, the promoter fragment containing sequences from −333 bp upstream to +106 downstream of the transcription start site had only 17%±1% of the activity of the full-length promoter. Thus, sequences for most of the SCBV promoter activity reside upstream of −333 bp from the transcription start site.

The portion of the SCBV promoter sequence capable of enhancing transcription driven by a heterologous minimal promoter sequence was examined. As defined by these experiments, an enhancer element is operationally identified as a short (200 to 300 bp) cis-acting DNA sequence, lacking a TATA-box, that, when placed 5' proximal to a heterologous minimal promoter sequence, increases the expression activity of the heterologous minimal promoter in a reproducible and measurable fashion when tested in either a transient or stable transformation system. Further, tandem duplications of the enhancer element provide even higher levels of expression activity of the heterologous minimal promoter than do single copies of the enhancer element. The heterologous minimal promoter element utilized in this Example comprises bases from −100 to +106 of a maize alcohol dehydrogenase1 (Adh1) gene promoter (corresponding to bases 997 to 1202 of GenBank Accession No. X04049, which is hereby incorporated by reference in its entirety).

Two fragments derived from the SCBV promoter, comprising sequences from −503 to −222 bp and from −758 to −222 bp relative to the transcription start site, were cloned 5' to sequences comprising a minimal maize Adh1 promoter fused to a coding region encoding a firefly luciferase (LUC) protein. Transcription of the chimeric genes was terminated by the Nos 3'UTR as described above. Maize Hi-II suspension culture cells were transformed by particle bombardment with DNAs of plasmids harboring LUC and GUS constructs, and enzymatic activities were measured and compared as above. Plasmids containing the LUC constructs having the −503 to −222 sequences or the −758 to −222 sequences placed 5' to the minimal Adh1 promoter showed 6-fold, and 4-fold, respectively, more LUC activity relative to the minimal Adh1 promoter without the added SCBV sequences. Thus, sequences within these fragments of the SCBV promoter enhance transcription activity mediated by a heterologous maize promoter.

Figure 3A:
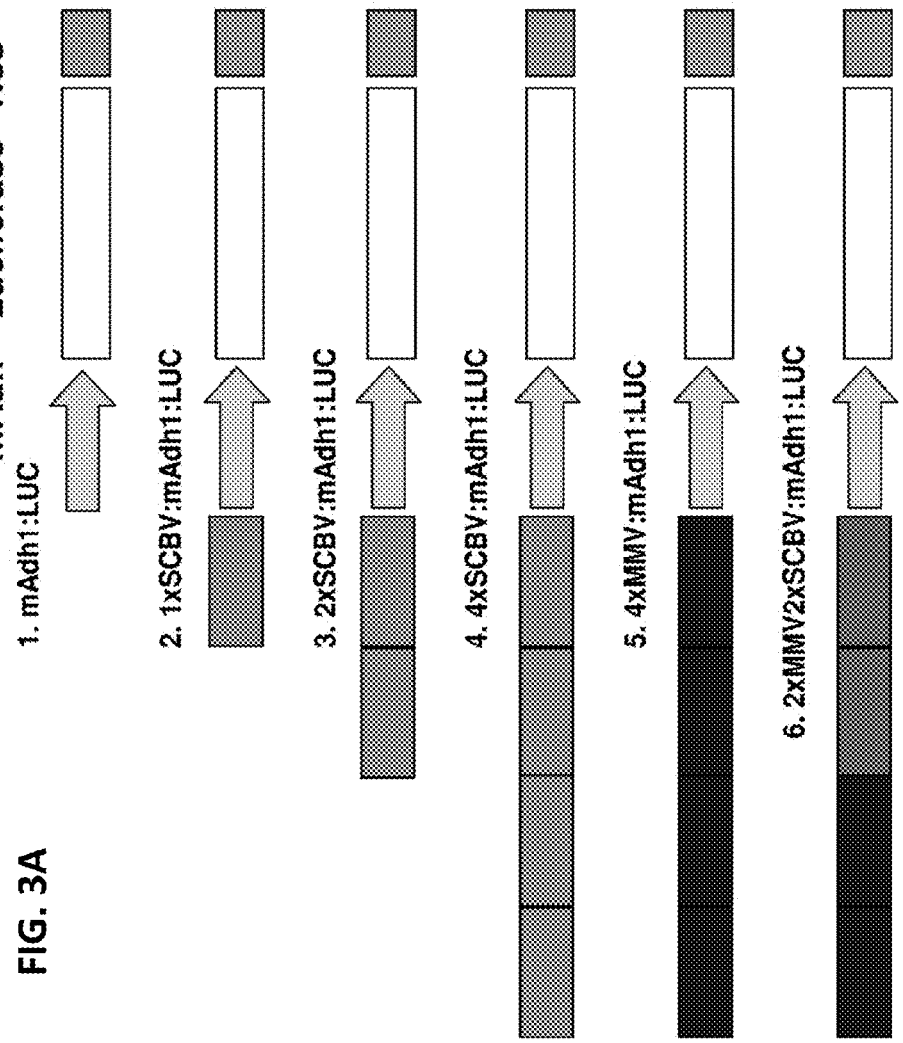
FIGS. 3A and 3B illustrate that the SCBV enhancer elements described herein enhance transcription from the maize Adh1 promoter. One, two and four copies of the SCBV promoter sequences from −503 to −222 were cloned upstream of a truncated maize Adh1 promoter, fused to the firefly luciferase gene (FIG. 3A). For comparison, 4 copies of the MMV enhancer sequences and 2 copies of the MMV enhancer and 2 copies of the SCBV promoter were cloned upstream of the truncated maize Adh1 promoter and fused to the firefly luciferase gene (FIG. 3A). These constructs were bombarded into maize Hi-II suspension cells along with the UBI::GUS reporter construct.
Figure 3B:
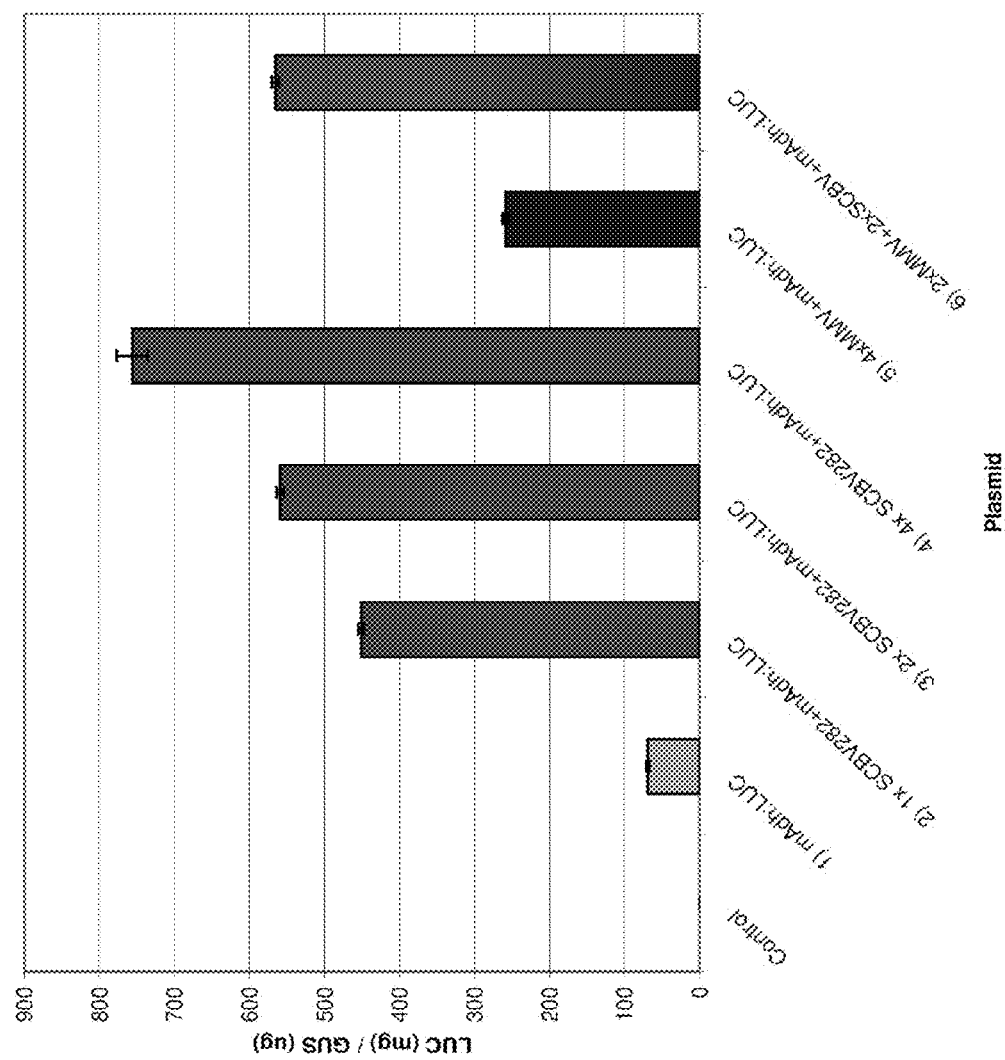
Figure 4:
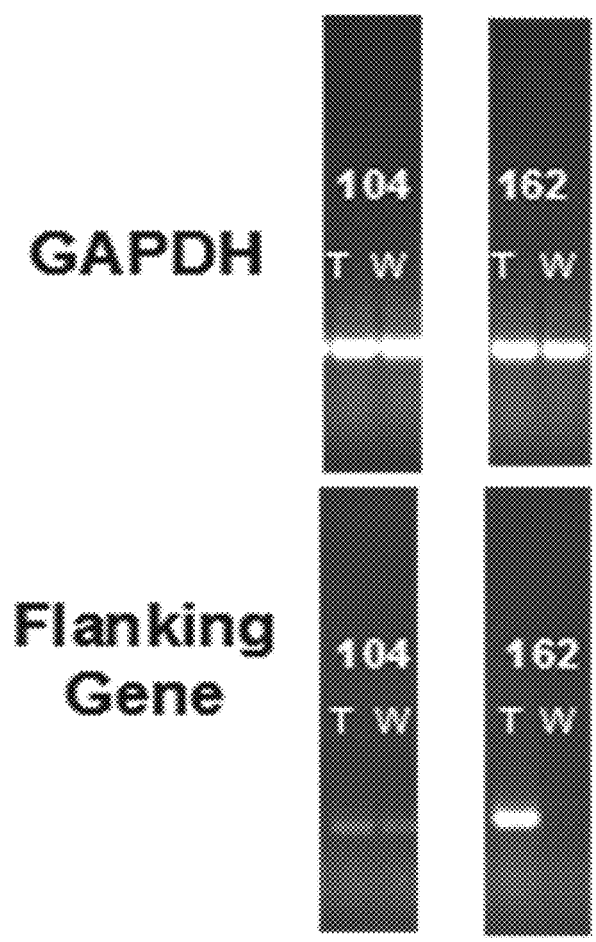
FIG. 4 shows accumulation of transcripts close to ("Flanking gene") the integration site of 4×SCBV in transgenic (T) plants compared non-transgenic (W) control plants, analyzed using reverse transcription and PCR(RT-PCR). The level of housekeeping gene GAPDH is shown for comparison. The 4×SCBV enhancer caused increased accumulation of transcripts of genes near where it integrates; this increase in transcript accumulation probably results from an increased rate of transcription.

The abilities of multiple copies of the −503 to −222 bp SCBV enhancer region to increase expression mediated by the minimal Adh1 promoter was tested by cloning one, two or four copies of the −502 to −222 bp sequences 5' to the minimal maize Adh1 promoter fused to the LUC coding region (FIG. 3A). Plasmid DNAs harboring the constructs (as well as plasmid DNA having a reference ubi1:GUS construct) were bombarded into maize Hi-II suspension culture cells, and LUC and GUS activities were measured and compared as above. Cells bombarded with constructs containing 1 copy, 2 copies, or 4 copies of the SCBV enhancer sequence region had more than 5 times, 6 times and 10 times, respectively, more LUC activity than did cells bombarded with an analogous minimal Adh1 promoter construct lacking SCBV enhancer sequences (FIG. 3B).

Nucleic acid bases comprising −502 to −222 bp of the SCBV promoter, as provided in SEQ ID NO: 1, encode transcriptional activation activity that can confer superior expression characteristics to a plant promoter. Further, transcriptional activation activity is increased by the stacking of multiple tandem copies of the bases comprising −502 to −222 bp of the SCBV promoter, as provided in SEQ ID NO: 1. Further still, the methods and reagents provided herein may be further examined and utilized to provide even shorter sequences that retain transcriptional activation activity, or may be combined with other transcriptional activator elements and plant promoters in new combinations.

Example 2

Transient Expression Testing of SCBV:LUC and ub1:GUS Constructs in Maize Hi-II Suspension Culture Cells This example describes transient expression testing of SCBV:LUC and ub1:GUS constructs in maize Hi-II suspension culture cells.

Maize Hi-II suspension culture cells (Armstrong et al., *Maize Genet. Coop. Newslett.*, 65:92-93, 1991) were transformed by particle bombardment with DNAs of plasmids harboring LUC and GUS constructs constructed as described above, and enzymatic activities were measured and compared. Bulk preparations of plasmid DNAs were prepared using QiAfilter™ Plasmid Maxi Kits (Qiagen, Germantown, Md.) and quantity and quality were analyzed using standard molecular methods.

Preparation of Maize Hi-II Suspension Culture Cells for Bombardment.

The Hi-II cells were maintained on a shaker at 125 rpm in H9CP+ medium at 28° in darkness (H9CP medium consists of MS salts 4.3 gm/L, sucrose 3%, Casamino acids 200 mg/L, myo-inositol 100 mg/L, 2.4-D 2 mg/L, NAA 2 mg/L, 1000× MS vitamins 1 mL/L, L-proline 700 mg/L, and coconut water (Sigma Aldrich, St. Louis, Mo.) 62.5 mL/L, pH 6.0). Prior to bombardment, the 2-day old Hi-II cultures were transferred to G-N6 medium (CHU N6 medium 3.98 g/L, CHU N6 vitamins 1 mL/L (both CHU components from PhytoTechnology Laboratories®, Lenexa, Kans.), Myo-inositol 100 mg/L, 2,4-D 2 mg/L and Sucrose 3%, pH 6.0) and allowed to grow for 24 hours. On the day of bombardment, the G-N6 grown cells (2.5 gm of cells) were transferred to sterile Whatman No. 1 filter disks (55 mm) placed on G-N6 medium containing 0.5 M D-sorbitol and 0.5 M D-mannitol and incubated for 4 hours. The osmotically adjusted cells are used for bombardment.

Preparation of Gold Particles with Plasmid DNAs and Bombardment Assay.

Gold particles (1 μm diameter, BioRad, Hercules, Calif.) were washed with 70% ethanol for 10 minutes, then three times with sterile water. The particles were dispensed in 50% glycerol at a concentration of 120 mg/mL. For a typical experiment, 150 μL (18 mg) of gold particles, approximately 5 μg of plasmid DNA, 150 μl it of 2.5 M $CaCl_2$ and 30 μL 0.2 M spermidine were combined. The reaction (total volume 375 μL) was incubated at room temperature for 10 minutes with occasional gentle vortexing. The DNA coated-gold particles were briefly centrifuged, washed with 420 μL of 70% ethanol and then with 420 μL of 100% ethanol. The final pellet was resuspended in 110 μL of 100% ethanol and subjected to a brief sonication (three bursts of 3 seconds each, with 1 minute between bursts) with a Branson 1450 sonicator. Aliquots of 12.2 μL of the gold-particles coated with DNA were spread on each of nine macrocarriers (BioRad, Hercules, Calif.) and used in bombardment assays using a BioRad PDS1000/He system. The suspension culture cells were transformed at a target distance of 9 cm using 3510 psi disks and each plate was bombarded 3 times. Following bombardment, the cells were incubated in the dark at 28° C., first for 12 hours on G-N6 containing D-sorbitol and D-mannitol medium, then on G-N6 plates for an additional 36 hours. Cells were collected from the plates, blotted to remove buffer and extracted with 300 µL of 2×CCLT LUC extraction buffer (Promega Corporation, Madison, Wis.). After centrifugation, about 600 µL of protein extract was collected. Protein concentrations were estimated using the Bradford assay.

LUC enzymatic activity (expressed in Luciferase Units (LU)/mg protein) and GUS enzymatic activity (expressed in GUS activity units (GU)/µg protein) were measured by methods found in, for example, Maliga et al. (*Methods in Plant Molecular Biology. A Laboratory Course Manual*. Cold Spring Harbor Laboratory Press, 1995). Relative activities of the test promoters in SCBV:LUC constructs were compared by normalizing LUC levels to GUS levels as the ratio of LUC/mg protein:GUS/µg protein.

Example 3

Plasmids for Activation Tagging in Maize Plants

This example describes generation of *Agrobacterium* superbinary plasmids.

The superbinary system is a specialized example of an *Agrobacterium* shuttle vector/homologous recombination system (Komari et al., *Meth. Mol. Biol.* 343:15-41, 2006; Komari et al., *Plant Physiol.* 114:1155-1160, 2007; see also European Patent No. EP604662B1 and U.S. Pat. No. 7,060,876 each of which is incorporated by reference in its entirety). The *Agrobacterium tumefaciens* host strain employed with the superbinary system is LBA4404(pSB1). Strain LBA4404 (pSB1) harbors two independently-replicating plasmids, pAL4404 and pSB1. pAL4404 is a Ti-plasmid-derived helper plasmid which contains an intact set of vir genes (from Ti plasmid pTiACH5), but which has no T-DNA region (and thus no T-DNA left and right border repeat sequences). Plasmid pSB1 supplies an additional partial set of vir genes derived from pTiBo542. One example of a shuttle vector used in the superbinary system is pSB11, which contains a cloning polylinker that serves as an introduction site for genes destined for plant cell transformation, flanked by right and left T-DNA border repeat regions. Shuttle vector pSB11 is not capable of independent replication in *Agrobacterium*, but is stably maintained therein as a co-integrant plasmid when integrated into pSB1 by means of homologous recombination between common sequences present on pSB1 and pSB11. Thus, the fully modified T-DNA region introduced into LBA4404(pSB1) on a modified pSB11 vector is productively acted upon and transferred into plant cells by Vir proteins derived from two different *Agrobacterium* Ti plasmid sources (pTiACH5 and pTiBo542). The superbinary system has proven to be particularly useful in transformation of monocot plant species (See Hiei et al., *Plant J.* 6:271-282, 1994, and Ishida et al., *Nat. Biotechnol.* 14:745-750, 1996).

A transformation plasmid for production of activation tagged maize plants can include a cointegrant plasmid formed by homologous recombination between the superbinary plasmid pSB1 and pEPP1088, having a pSB11 vector backbone (see European Patent No. EP604662B1 and U.S. Pat. No. 7,060,876 each of which are hereby incorporated by reference). The cointegrant plasmid is referred to as pSB1::pEPP1088 or as a ZeaTAG vector. The structure of pEPP1088 was validated by restriction enzyme analysis and DNA sequence determination of selected regions of the construct. pEPP1088 contains, positioned between Left (LB) and Right (RB) T-DNA border sequences provided by the pSB 11 plasmid, 4 copies of the −502 to −222 by SCBV enhancer sequences described above and a selectable marker gene comprised of a rice (*Oryza sativa*) actin gene promoter with associated intron 1 and 5' UTR (essentially as disclosed as bases 12 to 1411 of GenBank Accession No. EU155408.1 which is hereby incorporated by reference in its entirety), a coding sequence for an AAD-1 herbicide tolerance protein as disclosed in U.S. Patent Application No. 20090093366, and a 3' UTR terminator sequence from maize lipase gene essentially as disclosed as bases 921 to 1277 of GenBank Accession No. gb|L35913.1|MZELIPASE and in U.S. Pat. No. 7,179,902 each of which is hereby incorporated by reference in its entirety.

The T-DNA of pEPP1088 (and as present in pSB1::pEPP1088) integrates at random locations in maize chromosomes when introduced into maize cells by *Agrobacterium* mediated transformation. Selection for transformed maize cells is provided by the constitutively expressed AAD1 selectable marker gene in the T-DNA. The T-DNA carrying tandem copies of the potent −502 to −222 by SCBV transcriptional enhancer activator element causes aberrant expression of native genes nearby the integration site, thereby, in some instances, providing new identifiable traits to plants regenerated from the transformed tissues. Modern molecular biology methods are available which facilitate the isolation and identification of the affected genes near the acceptor site, thus providing the isolated genes for further exploitation.

Example 4

*Agrobacterium*-Mediated Transformation of Maize

This example describes generation of *Agrobacterium*-mediated transformation of maize Immature Embryo Production.

Seeds from a B104 inbred line were planted into 4-gallon-pots containing SUNSHINE CUSTOM BLEND® 160 growing mix (Sun Gro Horticulture, Bellevue, Wash.). The plants were grown in a greenhouse using a combination of high pressure sodium and metal halide lamps with a 16:8 hour Light:Dark photoperiod. To obtain immature embryos for transformation, controlled sib-pollinations were performed. Immature embryos were isolated at 10 to 13 days post-pollination when embryos were approximately 1.4 to 2.0 mm in size.

Infection and Co-Cultivation.

Maize ears were surface sterilized by immersing in 50% commercial bleach with Tween 20 (1 or 2 drops per 500 mL) for 10 minutes and triple-rinsed with sterile water. A suspension of *Agrobacterium* cells containing a superbinary vector cointegrant plasmid was prepared by transferring 1 or 2 loops of bacteria grown on YEP solid medium containing 50 mg/L Spectinomycin, 10 mg/L Rifampicin, and 50 mg/L Streptomycin at 28° C. for 3 days or 25° C. for 4 days into 5 mL of liquid infection medium (MS salts, ISU Modified MS Vitamins, 3.3 mg/L Dicamba, 68.4 gm/L sucrose, 36 gm/L glucose, 700 mg/L L-proline, pH 5.2) containing 100 µM acetosyringone. The solution was gently pipetted up and down using a sterile 5 mL pipette until a uniform suspension was achieved, and the concentration was adjusted to an optical density of 0.3 to 0.5 at 600 nm ($OD_{600}$) using an Ultrospec 10 Cell Density Meter (GE Healthcare/Amersham Biosciences, Piscataway, N.J.). Immature embryos were isolated directly into a micro centrifuge tube containing 2 mL of the infection medium. The medium was removed and replaced twice with 1 to 2 mL of fresh infection medium, then removed and replaced with 1.5 mL of the *Agrobacterium* solution. The *Agrobacterium* and embryo solution was incubated for 5 minutes at room temperature and then transferred to co-cultivation medium which contained MS salts, ISU Modified MS Vitamins, 3.3 mg/L Dicamba, 30 gm/L sucrose, 700 mg/L L-proline, 100 mg/L myo-inositol, 100 mg/L Casein Enzymatic Hydrolysate, 15 mg/L $AgNO_3$, 100 µM acetosyringone, and 2.3 to 3 gm/L Gelzan™ (Sigma-Aldrich, St. Louis, Mo.), at pH 5.8. Co-cultivation incubation was for 3 to 4 days at 25° C. under either dark or 24-hour white fluorescent light conditions (approximately 50 $\mu Em^{-2}s^{-1}$).

Resting and Selection.

After co-cultivation, the embryos were transferred to a non-selection MS-based resting medium containing MS salts, ISU Modified MS Vitamins, 3.3 mg/L Dicamba, 30 gm/L sucrose, 700 mg/L L-proline, 100 mg/L myo-inositol, 100 mg/L Casein Enzymatic Hydrolysate, 15 mg/L $AgNO_3$, 0.5 gm/L MES (2-(N-morpholino)ethanesulfonic acid monohydrate; PhytoTechnologies Labr., Lenexa, Kans.), 250 mg/L Carbenicillin, and 2.3 gm/L Gelzan™, at pH 5.8. Incubation was continued for 7 days at 28° C. under either dark or 24-hour white fluorescent light conditions (approximately 50 $\mu Em^{-2}s^{-1}$). Following the 7 day resting period, the embryos were transferred to selective medium. For selection of maize tissues transformed with a superbinary plasmid containing a plant expressible AAD1 selectable marker gene, the MS-based resting medium (above) was used supplemented with Haloxyfop. The embryos were first transferred to selection media containing 100 nM Haloxyfop and incubated for 1 to 2 weeks, and then transferred to 500 nM Haloxyfop and incubated for an additional 2 to 4 weeks. Transformed isolates were obtained over the course of approximately 5 to 8 weeks at 28° C. under either dark or 24-hour white fluorescent light conditions (approximately 50 $\mu m^{-2}s^{-1}$). Recovered isolates were bulked up by transferring to fresh selection medium at 1 to 2 week intervals for regeneration and further analysis.

Those skilled in the art of maize transformation will understand that other methods of selection of transformed plants are available when other plant expressible selectable marker genes (e.g., herbicide tolerance genes) are used.

Pre-Regeneration.

Following the selection process, cultures exposed to the 24-hour light regime were transferred to an MS-based pre-regeneration medium containing MS salts, ISU Modified MS Vitamins, 45 gm/L sucrose, 350 mg/L L-proline, 100 mg/L myo-inositol, 50 mg/L Casein Enzymatic Hydrolysate, 1 mg/L $AgNO_3$, 0.25 gm/L MES, 0.5 mg/L naphthaleneacetic acid, 2.5 mg/L abscisic acid, 1 mg/L 6-benzylaminopurine, 250 mg/L Carbenicillin, 2.5 gm/L Gelzan™, and 500 nM Haloxyfop, at pH 5.8. Incubation was continued for 7 days at 28° under 24-hour white fluorescent light conditions (approximately 50 $\mu Em^{-2}s^{-1}$).

Regeneration and Plantlet Isolation.

For regeneration, the cultures were transferred to an MS-based primary regeneration medium containing MS salts, ISU Modified MS Vitamins, 60 gm/L sucrose, 100 mg/L myo-inositol, 125 mg/L Carbenicillin, 2.5 gm/L GELZAN™ Gellan Gum, and 500 nM Haloxyfop, at pH 5.8. After 2 weeks at 28° under either dark or 24-hour white fluorescent light conditions (approximately 50 $\mu Em^{-2}s^{-1}$), tissues were transferred to an MS-based secondary regeneration medium composed of MS salts, ISU Modified MS Vitamins, 30 gm/L sucrose, 100 mg/L myo-inositol, 3 gm/L GELZAN™ (Gellan Gum), at pH 5.8, with, or without, 500 nM Haloxyfop. Regeneration/selection was continued for 2 weeks at 28° under either 16-hour or 24-hour white fluorescent light conditions (approximately 50 $\mu Em^{-2}s^{-1}$). When plantlets reached 3 to 5 cm in length, they were excised and transferred to secondary regeneration medium (as above, but without Haloxyfop) and incubated at 25° under 16-hour white fluorescent light conditions (approximately 50 $\mu Em^{-2}s^{-1}$) to allow for further growth and development of the shoot and roots.

Seed Production.

Plants were transplanted into METRO-MIX® 360 (soilless growing medium) (Sun Gro Horticulture) and hardened-off in a growth room. Plants were then transplanted into Sunshine Custom Blend 160 soil mixture and grown to flowering in the greenhouse. Controlled pollinations for seed production were conducted.

Example 5

SCBV Enhancer Activity in Stably Transformed Maize Cells

Genomic DNA was isolated (Qiagen DNeasy® Plant Mini Kit; Qiagen, Germantown, Md.) from ten $T_0$ plants regenerated from transformed B104 immature embryos, and the genomic locations of the integrated T-DNAs transferred from pSB1::pEPP1088 were determined by inverse PCR cloning and DNA sequencing of the inverse PCR amplified products. The identities of genes represented by the flanking coding regions positioned within 10 kb of the 4×SCBV enhancer were determined by BLAST searches (Altschul et al., *J. Mol. Biol.*, 215: 403-410, and Karlin et al., *Proc. Natl. Acad. Sci. USA* 87: 2264-2268, 1990) using the flanking sequences as query sequences. Analyses of the BLAST results revealed that the T-DNAs, and hence the 4×SCBV enhancers, were integrated at a different genomic location in each of the lines, and therefore the 4×SCBV enhancers are flanked by different genes in each line (Table 1).

Total RNA was isolated (Qiagen RNeasy® Plant Mini Kit, Qiagen, Germantown, Md.) from leaf tissues of the ten $T_0$ lines. Transcript accumulation of the identified flanking genes was compared between the appropriate $T_o$ plants and non-transformed control plants by reverse transcription and RT-PCR (Real Time PCR), using primers specific for the relevant genes flanking the 4×SCBV enhancers. As a control, transcript accumulation for the endogenous GAPDH gene was also determined.

RT-PCR products revealed increased accumulation of transcripts originating from 3 of the different flanking genes in these lines. The 4×SCBV enhancers are located 2.6 kb and 2.8 kb upstream of the affected flanking genes in 2 of the $T_0$ lines, and 478 by downstream of the affected flanking gene in the third $T_0$ line. Thus, these results indicate that the 4×SCBV enhancers delivered by T-DNA cause strand-independent increased accumulation of transcripts of genes nearby the integration site. Table 1 indicates the flanking genes identified and the results of analyses of their transcription levels.

TABLE 1

Effect 4XSCBV enhancer on the RNA accumulation of the flanking genes in 10 T0 plants.

| T0 Plant ID | Distance to the 4XSCBV (bp) | Flanking Gene Name | RNA Accumulation |
|---|---|---|---|
| ZT00031845 | 1197 | P-loop containing NTP hydrolases | No change |
| ZT00032132 | 5'-UTR | A protein that helps vesicular fusion proteins | No change |
| ZT00036435 | 2644 | DEAD-box-like helicase | Increased |
| ZT00034545 | 1972 | High mobility group-like nuclear protein | No change |
| ZT00036729 | EST | Unknown protein | No change |
| ZT00035749 | 2818 | Unknown protein (GRMZM2G115661) | Increased |
| ZT00033904 | 830 | Unknown protein | No change |
| ZT00036426 | 79 | Ribosomal protein L22/L17; T0 plant is tall | No change |
| ZT00036426 | 2150 | Signal peptide | No change |
| ZT00035050 | 478 from the 3'-end | Unknown gene (GRMZM2G139336) | Increased |

One skilled in the fields of maize genetics and plant molecular biology will realize that, depending upon the nature of the affected genes, the increased expression of adjacent genes induced by 4×SCBV enhancers will in some cases confer upon the transgenic plant new and valuable traits. Collectively, plants having the 4×SCBV enhancers represent a ZeaTAG-marked population. The traits may be the result of increased accumulation of the affected gene's encoded protein per se, as for example, increased accumulation of a nutritionally desirable protein in the seed, or the result of a downstream effect whereby the gene product of the immediately affected gene controls the expression of one or a multitude of other genes (as in the case of, for example, transcriptional activator/repressor genes). The random nature of integration location of introduced T-DNAs, coupled with standard plant breeding methods, may be used to establish large populations of plants comprising a library of T-DNA bearing plants having activator elements positioned within an effective distance of all or most genes within the maize genome, and thus provides the opportunity for all or most maize genes to be transcriptionally activated.

Plant-level screening for phenotypes of economic importance is possible under growth chamber, greenhouse, or field environments. As shown here, molecular biology methods such as inverse PCR enable the isolation of an integrated T-DNA and substantial lengths of genomic DNA flanking the integrated T-DNA from plants exhibiting a desirable phenotype. Further, methods such as genome walking techniques allow the determination of even more extensive regions of genomic DNA sequence, thus enabling identification of the genes present in proximity to introduced activator elements. High throughput methods such as microarray analysis and more gene specific analytical methods enable identification and quantification of affected transcript levels. Candidate genes involved in relevant agronomic traits may thus identified, isolated, and further characterized and exploited to provide new and valuable varieties of crops.

Conversely, the new trait may be the result of disruption of maize gene function due to the integration of the T-DNA having the 4×SCBV enhancers into the coding region or expression regulatory regions of the maize gene. If such is the case, the T-DNA having the 4×SCBV enhancers and surrounding genomic regions can be isolated and further characterized.

Example 6

Forward Genetic Screening of the ZeaTAG Population

This example describes forward genetic screening of the ZeaTAG population for altered phenotypes.

Drought Stress Screens

To identify ZeaTAG lines that contain mutations conferring drought tolerance, plants from individual ZeaTAG events are planted in a field. Water is withheld to cause drought stress during the reproductive phase of the growth cycle; roughly 2 weeks prior to flowering to approximately 2 weeks after flowering. The target is to achieve 4 weeks of stress period at flowering stage. Environmental modeling is used to predict accurate corn evapotransporation demand based on soil moisture monitoring and weather data (air temperature, vapor pressure deficit, wind speed, and net radiation). Plants are monitored for drought symptoms such as leaf rolling by visual observation, increased leaf temperature by infrared thermometers, reduced photosynthesis by chlorophyll fluorescence and reduced yield by measuring grain production. Plants that show significantly less leaf rolling, lower leaf temperature, higher rates of photosynthesis or have significantly more yield under water stress conditions are identified and used in subsequent screens.

ZeaTAG events displaying significantly more drought tolerance are planted in a replicated field trial to confirm the drought tolerant phenotype. These events are planted in a randomize split block design with at least 3 replications. One block is irrigated with water sufficient to prevent water stress. The other block is grown under water deficient conditions as described above. Plants are monitored for leaf rolling, increased leaf temperature, decreased photosynthesis and decreased yield as described above. Plants with significantly less leaf rolling, lower leaf temperature, greater photosynthesis or greater yield than untransformed control plants are considered to have passed the secondary screen.

Nitrogen Use Efficiency Screens

To identify ZeaTAG events with greater nitrogen use efficiency than non-transgenic control plants a primary screen is performed. Plants containing approximately 40,000 ZeaTAG containing events are grown in the field under nitrogen deficient conditions. Plants are grown in fields with less than 35 lbs of N per acre. Plants are monitored for chlorosis by visual inspection, increased leaf temperature by infrared thermometers, and decreased yield by grain harvest. These parameters are compared with non-transgenic control plants. ZeaTAG lines showing less chlorosis, lower leaf temperature, higher photosynthetic rates or greater yields than non-transgenic control lines are evaluated in secondary screens.

As a secondary screen, ZeaTAG events displaying significantly more nitrogen use efficiency are planted in a replicated field trial to confirm the phenotype. These events are planted in a randomize split block design with at least 3 replications. One block is irrigated with sufficient nitrogen fertilizer to prevent nitrogen stress. The other block is grown under nitrogen deficient conditions as described above. Plants are monitored for chlorosis by visual inspection, increased leaf temperature by infrared thermometers, and decreased yield by grain harvest. Plants with significantly less chlorosis, lower leaf temperature, greater photosynthesis or greater yield than untransformed control plants are considered to have passed the secondary screen.

Once the phenotype has been confirmed in the secondary screen, the phenotype is tested for genetic linkage with the ZeaTAG insertion by screening the progeny of a cross between the non-transformed parental line and the ZeaTAG line. When plants containing the ZeaTAG element display the phenotype and plants that do not contain the ZeaTAG element do not, the phenotype is considered to be genetically linked with the insert and likely to be caused by the ZeaTAG element. To identify genes whose expression may be affected by the ZeaTAG element, the location of the ZeaTAG element within the genome is determined.

The genomic location of the ZeaTAG element is determined by isolating genomic sequences flanking the ZeaTAG element and comparing these sequences to the genomic sequence of maize. Sequences flanking the ZeaTAG element can be determined by a number of molecular biological techniques, including but not limited to, inverse PCR (iPCR) (Ochman et al., *Genetics,* 120: 621-6231988), TAIL (Liu et al., *Plant Journal* 8: 457-463, 1995) and ligation-mediated PCR (LMPCR) Prod'hom et al., *FEMS Microbiol Lett.* 158: 75-81, 1998). These sequences are compared to genomic sequences by sequence alignment tools such as BLAST to identify the location of the ZeaTAG element within the genome.

Genes flaking or interrupted by the ZeaTAG element are determined by examining the annotated genome. Transcription of genes flanking the ZeaTAG element may be responsible for the mutant phenotype. These genes may be overexpressed in wild-type maize to test whether they can confer a similar phenotype. To test this, the genes are cloned into transformation vectors driven by strong promoters or by their own promoter with enhancer sequences flanking them to enhance transcription. These vectors are introduced into wild-type maize by transformation and plants resulting from this transformation are tested for the phenotype.

Similarly, genes interrupted by the ZeaTAG element may cause the phenotype. To confirm that a gene interrupted by the element is responsible for the phenotype, expression of the gene can be disrupted and plants containing this disruption can be tested for the phenotype. The disruption of expression of specific genes can be accomplished by a number of methods know to those skilled in the art including but not limited to antisense RNA, artificial micro RNAs and identifying mutations in the gene by TILLING.

Example 7

Reverse Genetic Screening of the ZeaTAG population

This example describes reverse genetic screening of the ZeaTAG population for mutations.

Reverse genetic screening is looking for mutations affecting specific genes and subsequently testing the identified line for a mutant phenotype. The ZeaTAG population can be used in reverse genetic analyses in several ways including but not limited to generating a collection Flanking Sequence Tags for the population (Jeong et al., *The Plant Journal* 45: 123-132, 2006) and generating an indexed collection of pooled samples of DNA from the ZeaTAG population (May et al., *Molecular Biotechnology* 20: 209-221, 2002).

A collection of Flanking Sequence Tags is generated by sampling leaf tissue from the ZeaTAG population, isolating DNA from each, identification of sequences flanking the insert and storing the sequences in a searchable database where the sequences are linked to the events from which they came. Genomic DNA is isolated using the Qiagen DNAeasy Plant Kit (Qiagen, Germantown, Md.) using the protocol recommended by the manufacturer. Sequences flanking the insert are identified using Ligation Mediated PCR (Mueller et al., *Science* 246: 780-786, 1989) as modified by Yephremov and Saedler (*Plant Journal* 21: 295-305, 2000). Briefly, genomic DNA from a ZeaTAG line is fragmented restriction enzyme digestion and denatured. A biotinlyated oligonucleotide primer complementary to the sequence at the end of the ZeaTAG element is hybridized to the fragmented DNA and extended by DNA polymerase. Streptavidin coated magnetic beads are added to the mixture to bind DNA fragments containing DNA fragments extended from this primer. A double-stranded DNA adaptor of known sequence is ligated to the unknown end. These fragments are PCR amplified using oligonucleotides complementary to sequences within the ZeaTAG element and the DNA adaptor at the other end. The sequence of the PCR fragment is then determined and mapped to the maize genomic sequence by BLAST. These sequences locate the site of insertion of the ZeaTAG element. Genes within a ~10 kbp may be up-regulated by the enhancer sequences within the ZeaTAG element.

Plants containing insertions in or near genes that are hypothesized to cause a phenotype can be identified by searching the database. Plants containing these events can be tested for the phenotype.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A chimeric transcription regulatory region comprising:
   a sugarcane bacilliform viral (SCBV) enhancer element consisting of position 337 to position 618 of SEQ ID NO: 1; and
   operably linked thereto, a heterologous promoter comprising an RNA polymerase binding site and a mRNA initiation site,
   wherein the chimeric transcription regulatory region enhances transcription of an operably linked nucleotide sequence of interest, compared to transcription of the nucleotide sequence of interest operably linked to a chimeric transcription regulatory region comprising the promoter and not comprising the SCBV enhancer sequence.

2. The chimeric transcription regulatory region of claim 1, further comprising two or more copies of the sugarcane bacilliform viral (SCBV) enhancer element consisting of position 337 to position 618 of SEQ ID NO: 1.

3. The chimeric transcription regulatory region of claim 1, wherein the promoter is obtained from the upstream region of a plant virus gene, a bacterial gene, a fungal gene, a plant nuclear gene, a plant extra-nuclear gene, an invertebrate gene, or a vertebrate gene.

4. A construct comprising the transcription regulatory region of claim 1 operably linked to a transcribable polynucleotide molecule operably linked to a 3' transcription termination polynucleotide molecule.

5. The construct of claim 4, wherein said transcribable polynucleotide molecule confers an agronomic trait to a plant in which it is expressed.

6. A transgenic plant stably transformed with the construct of claim 4.

7. The transgenic plant of claim 6, wherein the transcribable polynucleotide molecule confers an agronomic trait to a plant in which it is expressed.

8. A seed of the transgenic plant of claim 6, wherein the seed comprises the construct.

9. The transgenic plant of claim 6, wherein the plant is a maize plant.

10. A transgenic plant cell comprising the chimeric transcription regulatory region of claim 1.

11. A method of producing a transgenic plant comprising:
    (i) transforming a plant cell or tissue with the construct of claim 4; and
    (ii) regenerating the transgenic plant from the transformed plant cell or tissue, thereby producing a transgenic plant.

12. The method of claim 11, wherein the transgenic plant is a dicotyledon.

13. The method of claim 11, wherein the transgenic plant is a monocotyledon.

14. A plant cell or tissue transformed with the construct of claim 4.

15. The plant cell or tissue of claim 14, wherein the plant cell or tissue is from a dicotyledon.

16. The plant cell or tissue of claim 14, wherein the plant cell or tissue is derived from a monocotyledon.

17. A transgenic plant cell, fruit, leaf, root, shoot, flower, seed, cutting or other reproductive material useful in sexual or asexual propagation, transgenic progeny plant inclusive of an F1 hybrid, transgenic male-sterile plant or any other transgenic plant or transgenic plant product, derivable from the transgenic plant of claim 5, wherein the transgenic plant cell, fruit, leaf, root, shoot, flower, seed, cutting or other reproductive material useful in sexual or asexual propagation, transgenic male-sterile plant, or other transgenic plant, or transgenic plant product comprises the construct.

18. A maize plant cell, tissue or plant comprising two or more copies of the sugarcane bacilliform viral (SCBV) enhancer element consisting of position 337 to position 618 of SEQ ID NO: 1, in which the two or more copies of the SCBV enhancer element is inserted into a genome of the maize plant cell, tissue or plant at a random location.

19. The maize plant cell, tissue or plant of claim 18, wherein the SCBV enhancer imparts enhanced transcription of a nucleotide sequence of interest which is under regulatory control of the SCBV enhancer and a promoter, as compared to transcription of the nucleotide sequence of interest in the absence of the SCBV enhancer.

20. The chimeric transcription regulatory region of claim 2, comprising at least three copies of the SCBV enhancer element.

21. The chimeric transcription regulatory region of claim 2, comprising at least four copies of the SCBV enhancer element.

* * * * *

SEQUENCE LISTING

```
<160> NUMBER OF SEQ ID NOS: 1

<210> SEQ ID NO 1
<211> LENGTH: 839
<212> TYPE: DNA
<213> ORGANISM: Sugarcane bacilliform virus

<400> SEQUENCE: 1
aagcttattg aatggggaaa acaaattctt gatccattcc ccaaattcaa gaaggatatg      60
```

```
tttgaaagaa ctgaacatat catgatggca acacaagagc ctacgctact atgtggatgc    120
aggaagcctg caatcatgtt aacatcagga acaaggctta atcctcgtag aagattttac    180
aagtgtgcca tgaatatctg ccactgctgg tattgggcag atttacttga agaatacgtg    240
caagagagga tcgaagattt catggttgaa aacttcgaca agaaagcaaa gctggatgaa    300
ccaagttcat caaacgttca ccatgatgat tatgaagaac accgttcgag tgtcatcgac    360
aggccaaggc caacagatga tcatttcaga ccatgggggg atgttacata ctggctgaat    420
aaagaagcag aagagtgcca cacaaggggc gacaacgtcg aaggcgcaga agacgcagtc    480
gatctcactg acgtaagcaa tgacgaccag tggaggagat cgtaagcaat gacgtatgga    540
gcgtggagga cccatgaaag cactgagaag gcatctcaac tttcggtgtg tgagtgcgca    600
tcctatgcga tgctttgtac ctttgttagc tgtgtgtgtc cttttggcat ctgtgccact    660
ttacctttgt cggccacgtt gcctttgctt agcatctacg caagcatagc gctcggctgg    720
tgtgtgttcc ctctgcctat ataaggcatg gttgtatgac tcttacactc atcggtagtt    780
caccacatga gtatttgagt caagtttggc ttgaataata agaattacac ctttccgca    839
```